(12) United States Patent
Gadek

(10) Patent No.: US 12,214,079 B2
(45) Date of Patent: *Feb. 4, 2025

(54) MICRONIZED LIPIDS

(71) Applicant: MCAL Therapeutics Inc., Park City, UT (US)

(72) Inventor: Thomas Gadek, Park City, UT (US)

(73) Assignee: MCAL Therapeutics Inc., Park City, UT (US)

( * ) Notice: Subject to any disclaimer, the term of this patent is extended or adjusted under 35 U.S.C. 154(b) by 226 days.

This patent is subject to a terminal disclaimer.

(21) Appl. No.: 17/306,244

(22) Filed: May 3, 2021

(65) Prior Publication Data

US 2022/0362154 A1 Nov. 17, 2022

(51) Int. Cl.
| | | |
|---|---|---|
| *A61K 9/127* | (2006.01) | |
| *A61K 9/00* | (2006.01) | |
| *A61K 47/02* | (2006.01) | |
| *A61K 47/26* | (2006.01) | |
| *A61K 47/36* | (2006.01) | |

(52) U.S. Cl.
CPC .......... *A61K 9/1272* (2013.01); *A61K 9/0048* (2013.01); *A61K 47/02* (2013.01); *A61K 47/26* (2013.01); *A61K 47/36* (2013.01)

(58) Field of Classification Search
CPC .... A61K 9/1272; A61K 9/0048; A61K 47/02; A61K 47/26; A61K 47/36; A61K 9/0014; A61K 9/10; A61K 47/44; A61K 47/14
USPC ....................................................... 424/451
See application file for complete search history.

(56) References Cited

U.S. PATENT DOCUMENTS

| | | | |
|---|---|---|---|
| 5,004,598 A * | 4/1991 | Lochhead | A61K 47/32 514/939 |
| 5,558,653 A | 9/1996 | Lindstrom | |
| 5,578,020 A | 11/1996 | Mosley | |
| 5,667,800 A * | 9/1997 | De Vringer | B82Y 5/00 424/78.02 |
| 5,810,794 A | 9/1998 | Peplinski | |
| 6,736,802 B1 | 5/2004 | Recanati | |
| 7,527,613 B2 | 5/2009 | Gaynes | |
| 7,563,256 B2 | 7/2009 | Hearne | |
| 7,846,140 B2 | 12/2010 | Hagele | |
| 9,289,494 B2 | 3/2016 | Albert et al. | |
| 9,545,333 B2 | 1/2017 | Alam et al. | |
| 9,999,540 B2 | 6/2018 | Yang et al. | |
| 10,265,214 B2 | 4/2019 | Shulman | |
| 10,507,132 B2 | 12/2019 | Graf et al. | |
| 2003/0108626 A1* | 6/2003 | Benita | A61K 9/0048 424/731 |

FOREIGN PATENT DOCUMENTS

EP 0 506 197 * 6/1998

OTHER PUBLICATIONS

Buchi. Spray Drying & Encapsulaiton Solutions. Downloaded from the internet Jun. 7, 2023. 24 pages.
Chhadva et al., Meibomian Gland Disease: The Role of Gland Dysfunction in Dry Eye Disease. Ophthalmology. Nov. 2017;124(11S):S20-S26.
Tatematsu et al., Mucosal microvilli in dry eye patients with chronic GVHD. Bone Marrow Transplant. Mar. 2012;47(3):416-25.
Veeregowda et al., Role of structure and glycosylation of adsorbed protein films in biolubrication. PLoS One. 2012;7(8):e42600.
Yanez-Soto et al., Interfacial phenomena and the ocular surface. Ocul Surf. Jul. 2014;12(3):178-201.

* cited by examiner

*Primary Examiner* — Frederick F Krass
*Assistant Examiner* — Lucy M Tien
(74) *Attorney, Agent, or Firm* — Casimir Jones, S.C.; J. Mitchell Jones

(57) ABSTRACT

The present invention relates to drug delivery vehicles comprising micronized particles that include an active lipid agent, and in particular to micronized lipid particles that comprise an ether lipid such as sn-1-O-eicosanyl-sn-2-palmitoyl-glycerol and its isomers.

30 Claims, 7 Drawing Sheets

Synthetic method for MCAL-201

$Dv_{50}$ 3.58 microns
$Dv_{90}$ 6.40 microns
Dynamic Light Scattering measurement of MCAL-201 micronized solid size distribution following jet milled micronization demonstrating particle sizes between 1 and 10 μm.

FIG. 3

Stably suspended formulations of MCAL-201 micronized solid (1-10 μm particle size, See FIG. 2) MCAL-201 in PBS, polysorbate 80 (3% w/w) and xanthan gum (0.125% to 0.25%) after 2 months of storage at room temperature.

Ratio of integrated peak areas for 1,3-EPRG isomer of MCAL-201 after micronization (See Fig. 2). 1,3 EPRG mole % = 1,3 isomer peak area divided by total 1,2 and 1,3 isomer peak areas (0.0233/ 2.0233 = 1.15 mol% 1,3 EPRG isomer of MCAL-201 in micronized MCAL-201).

Ratio of integrated peak areas for 1,3-EPRG isomer of MCAL-201 after 6 weeks storage of the solid micronized suspension at room temperature. 1,3 EPRG mole % = 1,3 isomer peak area divided by total 1,2 and 1,3 isomer peak areas (0.0200/ 2.0200 = 0.990 mol% 1,3 EPRG isomer of MCAL-201 in micronized MCAL-201).

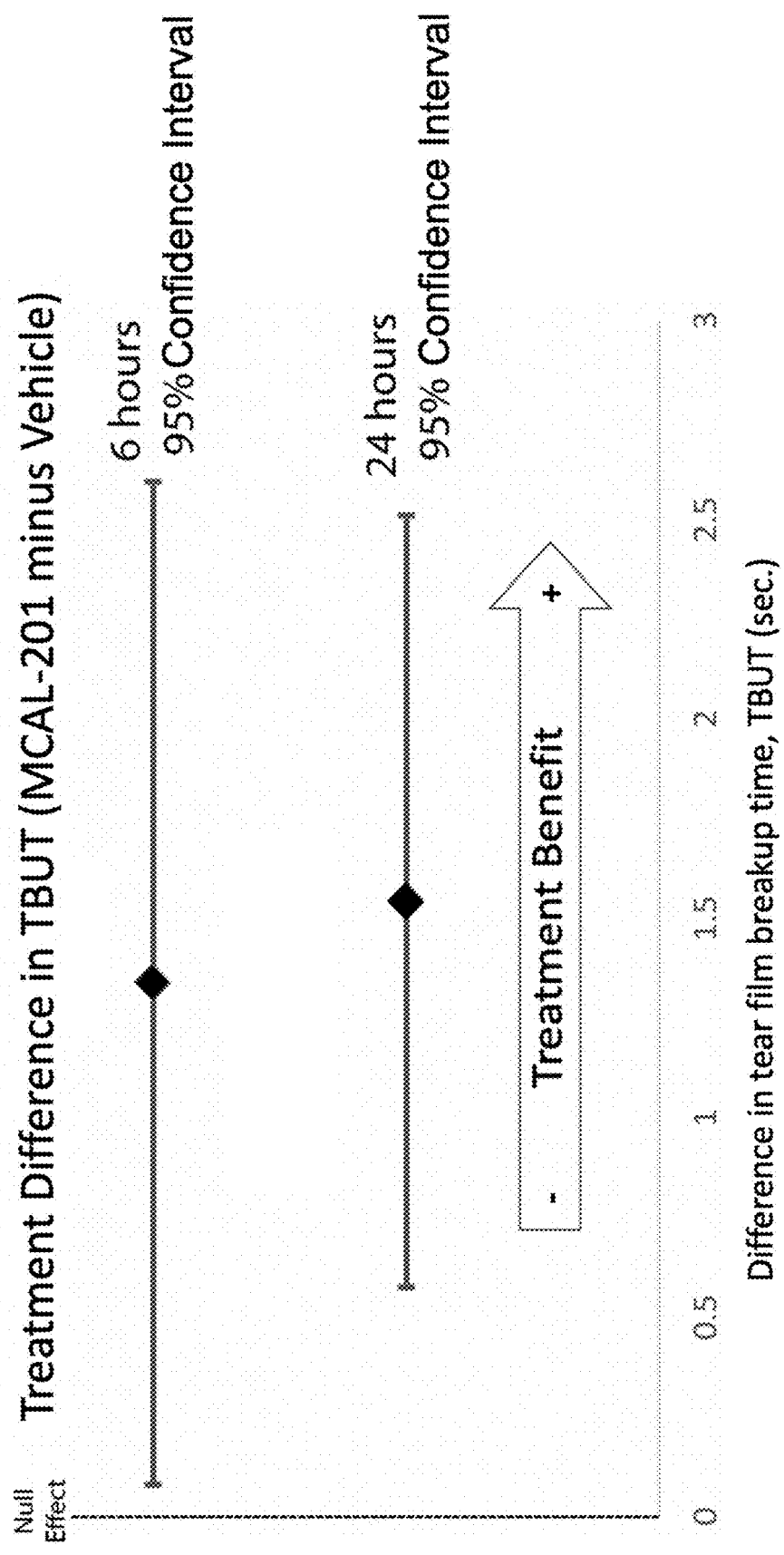

FIG. 6

Forest plot showing Treatment Difference in mean changes from baseline (MCAL-201 minus Vehicle) for tear film breakup time, TBUT, at 6 and 24 hours following a single 3 mg/mL dose of micronized solid MCAL-201 ophthalmic suspension in normal dogs. Since 95% Confidence Interval does not include the Null Hypothesis (Null Effect vertical dashed line at Zero), the Treatment Differences are statistically significant at $p < .05$ at both 6 and 24 hours. (N=5 dogs, 10 eyes, 3 measurements per eye at each timepoint (baseline, 6 hours and 24 hours)).

Stereospecific numbering, *sn*- glycerol numbering system..

MICRONIZED LIPIDS

FIELD OF THE INVENTION

The present invention relates to drug delivery vehicles comprising micronized particles that include an active lipid agent, and in particular to micronized lipid particles that comprise an ether lipid such as sn-1-O-eicosanyl-sn-2-palmitoyl-glycerol and its isomers.

BACKGROUND OF THE INVENTION

Dry eye syndrome is caused by a chronic lack of sufficient lubrication and moisture on the surface of the eye. Consequences of dry eyes range from subtle but constant eye irritation to significant inflammation and even scarring of the front surface of the eye. A major form of dry eye, evaporative dry eye is linked to meibomian gland dysfunction, where tear film lipid layer insufficiency and instability may result in increased evaporation and tear film instability, among other sequelae. Thus, evaporative dry eye, meibomian gland dysfunction and resulting tear film instability contribute to both the insufficient lubrication and insufficient moisture on the ocular surface in dry eye. For a review, see Chadya et al., Meibomian gland disease: the role of gland dysfunction in dry eye disease, Ophthalmology. 2017 Nov.; 124 (11 Suppl): S20—S26, which is incorporated by reference herein in its entirety.

In addition to being called dry eye syndrome, dry eye disease, or simply "dry eye," alternative medical terms used to describe dry eye. Keratitis sicca refers to dryness and inflammation of the cornea. Keratoconjunctivitis sicca refers to dry eye that affects both the cornea and the conjunctiva.

Dry eye syndrome is one of the most common eye conditions worldwide and a primary reason for visits to the eye doctor. In a review published in the Journal of Global Health, researchers reported that studies have shown the prevalence of dry eyes ranges from 5 percent to as high as 50 percent in different populations across the world. Risk factors for dry eye syndrome included advanced age, female sex, and computer use. Symptoms of dry eye syndrome include: burning sensation; itchy eyes; aching sensations; heavy eyes; fatigued eyes; sore eyes; dryness sensation; red eyes; photophobia; and blurred vision. Clinical signs of dry eye include decreased tear production as measured by the Schirmer tear test, defects in the integrity of the corneal epithelium as measured by vital staining (e.g., fluorescein) of the cornea and particularly instability of the tear film including instability of the tear film lipid layer as measured in a reduction in the tear film breakup time (TBUT).

Tear is comprised of aqueous, mucin and lipid components. With each and every blink, the aqueous and lipid components are intimately mixed and the aqueous and lipid components self sort into the inner aqueous and outer lipid layers of the tear film. Within the lipid layer, polar and nonpolar lipids self sort with the polar lipids forming a monolayer at the aqueous layer interface and the non-polar lipids forming a thicker outer layer of the tear film lipid layer which directly interfaces with air. The non-polar outer layer of the tear film lipid layer (TFLL) can be from 5 to 50 molecules thick. An adequate and consistent layer of tear on the surface of the eye is essential to keep the eyes healthy, comfortable and seeing well. The tear film bathes the eye's surface to keep it moist and wash away dust, debris and microorganisms that could damage the cornea and lead to an eye inflammation and/or infection. As noted, a normal tear film consists of three important components: an oily (lipid) component; a watery (aqueous) component; and a mucous-like (mucin) component. Each component of the tear film serves a critical purpose. For example, tear lipids help keep the tear film aqueous layer from evaporating too quickly and increase lubrication, while mucins (soluble and cell associated) help anchor and spread the tears across the living surface of the corneal epithelium. The aqueous component is the thickest layer of the precorneal tear film and contains a variety of proteins including immunoglobulins and lysozyme that serve in preventing microbial colonization. The tear film is described in Yanez-Soto et al., Interfacial phenomena and the ocular surface, Ocul Surf 2014 Jul.;12 (3):178-201, which is incorporated herein by reference in its entirety.

Each tear component is produced by different glands on or near the eye. The oily component is produced by meibomian glands in the eyelids as well as from harderian glands in species that possess one (e.g. rabbits). The aqueous component is produced by lacrimal glands located behind the outer aspect of the upper eyelids (in humans). Many vertebrate species also possess accessory lacrimal glands (e.g., the accessory lacrimal gland associated with the third eyelid of dogs). The soluble mucin component is produced by goblet cells in the conjunctiva that covers the white of the eye (sclera). A problem with any of these sources of tear film components can result in tear instability and dry eye.

What is needed in the art are effective treatments for dry eye, as well as effective delivery systems for those treatments.

SUMMARY OF THE INVENTION

The present invention relates to drug delivery vehicles comprising micronized particles that include an active lipid agent, and in particular to micronized lipid particles that comprise an ether lipid such as sn-1-O-eicosanyl-sn-2-palmitoyl-glycerol and its isomers, analogs and homologs as both the drug delivery vehicle and active lipid agent.

In some preferred embodiments, the present invention provides a drug delivery vehicle comprising crystalline and amorphous solid micronized lipid particles having an average particle size of less than 100 microns, the particles comprising an active agent and wherein the drug delivery vehicle is selected from the group selected from a therapeutic composition, a physiologically compatible carrier and a medical insert device.

In a first aspect, the present invention provides a lipid particle composition comprising solid non-polar lipid particles comprising an active lipid agent and having an average particle size of less than 50 microns stably suspended in a buffered aqueous vehicle suitable for topical administration.

In some preferred embodiments, the solid non-polar lipid particles have a melting point of less than 80 degrees C. In some preferred embodiments, the solid non-polar lipid particles have a melting point of from 20 to 80 degrees C. In some preferred embodiments, the solid non-polar lipid particles have a melting point of from 30 to 60 degrees C. In some preferred embodiments, the solid non-polar lipid particles have an average particle size of less than 20 microns. In some preferred embodiments, the solid non-polar lipid particles have an average particle size of less than 10 microns.

In some preferred embodiments, the active lipid agent is a non-polar ether lipid.

In some preferred embodiments, the solid non-polar lipid particles comprise an active lipid agent selected from the group consisting of:

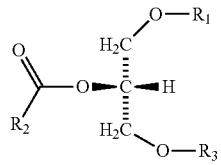

wherein
$R_1$ is an unsubstituted C6 to C30 alkyl or alkenyl;
$R_2$ is an unsubstituted C5 to C29 alkyl or alkenyl; and
$R_3$ is a hydrogen (i.e., H);

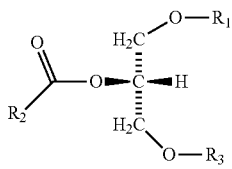

wherein
$R_1$ is a hydrogen (i.e., H);
$R_2$ is an unsubstituted C5 to C29 alkyl or alkenyl; and
$R_3$ is an unsubstituted C6 to C30 alkyl or alkenyl; and

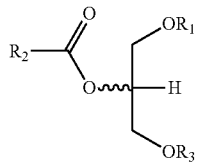

wherein
$R_1$ is an unsubstituted C6 to C30 alkyl or alkenyl;
$R_2$ is an unsubstituted C5 to C29 alkyl or alkenyl; and
$R_3$ is a hydrogen (i.e., H).

In some preferred embodiments, the solid non-polar lipid particles comprise an active lipid agent selected from the group consisting of:

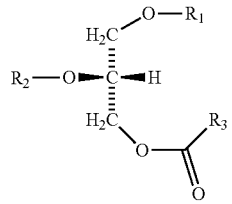

wherein
$R_1$ is an unsubstituted C6 to C30 alkyl or alkenyl;
$R_2$ is a hydrogen (i.e., H); and
$R_3$ is an unsubstituted C5 to C29 alkyl or alkenyl;

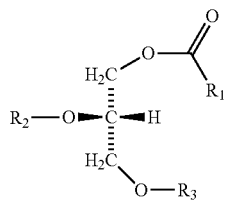

wherein
$R_1$ is an unsubstituted C5 to C29 alkyl or alkenyl;
$R_2$ is a hydrogen (i.e., H); and
$R_3$ is an unsubstituted C6 to C30 alkyl or alkenyl; and

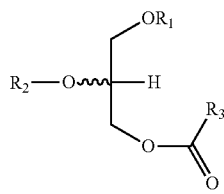

wherein
$R_1$ is an unsubstituted C6 to C30 alkyl or alkenyl;
$R_2$ is a hydrogen (i.e., H); and
$R_3$ is an unsubstituted C5 to C29 alkyl or alkenyl.

In some preferred embodiments, the solid non-polar lipid particles comprise an active lipid agent selected from the group consisting of 1-O-eicosanyl-2-palmitoyl-rac-glycerol (1,2-EPRG), sn-1-O-eicosanyl-2-palmitoyl-glycerol, sn-2-palmitoyl-3-O-eicosanyl-glycerol, 1-O-eicosanyl-3-palmitoyl-rac-glycerol (1,3-EPRG), sn-1-O-eicosanyl-3-palmitoyl-glycerol, sn-1-palmitoyl-3-O-eicosanyl-glycerol and mixtures thereof. In some preferred embodiments, the solid non-polar lipid particles comprise an active lipid agent selected from the group consisting of 1-O-eicosanyl-2-palmitoyl-rac-glycerol (1,2-EPRG) or 1-O-eicosanyl-3-palmitoyl-rac-glycerol (1,3-EPRG) and mixtures thereof.

In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 95% (mole percent) of the 1-O-eicosanyl-2-palmitoyl-rac-glycerol (1,2-EPRG) isomer or greater than 95% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer or greater than 98% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer or greater than 99% (mole percent) of the 1-O-eicosanyl-3-palmitoyl-rac-glycerol (1,3-EPRG) isomer.

In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 50%

(mole percent) of the 1-O-eicosanyl-2-palmitoyl-rac-glycerol (1,2-EPRG) isomer and no greater than 50% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising no greater than 50% (mole percent) of the 1-O-eicosanyl-2-palmitoyl-rac-glycerol (1,2-EPRG) isomer and more than 50% (mole percent) of the 1-O-eicosanyl-3-palmitoyl-rac-glycerol (1,3-EPRG) isomer.

In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 95% (mole percent) of the 1-O-eicosanyl-2-palmitoyl-rac-glycerol (1,2-EPRG) isomer and no greater than 5% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer and no greater than 2% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer and no greater than 1% (mole percent) of the 1-O-eicosanyl-3-palmitoyl-rac-glycerol (1,3-EPRG) isomer.

In some preferred embodiments, the solid non-polar lipid particles further comprise one or more additional lipids selected from the group consisting of a nonpolar mono-, di- or tri- glyceride, a wax ester including cholesterol esters, a sterol, a free fatty acid and combinations thereof. In some preferred embodiments, the aqueous buffered vehicle comprises phosphate buffered saline (PBS), 3% or less (w/w of the vehicle) polysorbate 80 and 0.3% or less (w/w of the vehicle) xanthan gum and has a pH of from 6.5-8.0 and an osmolality of from 260 to 320 mOsm/L.

In some preferred embodiments, the suspended particles are stable to phase separation from the suspension for 6 months at room temperature. In some preferred embodiments, the suspended particles are chemically stable to <5% isomerization of 1,2-EPRG to the isomeric 1,3-EPRG during storage at room temperature for 6 months. In some preferred embodiments, the suspended particles are stable to phase separation from the suspension for 24 months at room temperature. In some preferred embodiments, the suspended particles are chemically stable to <5% isomerization of 1,2-EPRG to the isomeric 1,3-EPRG during storage at room temperature for 24 months.

In some preferred embodiments, the composition is sterile. In some preferred embodiments, the composition comprises a preservative. In some preferred embodiments, the suspension is preservative-free. In some preferred embodiments, the aqueous buffered vehicle is an ophthalmologically acceptable carrier. In some preferred embodiments, the aqueous buffered vehicle further comprises an agent selected from the group consisting of a buffering agent, a tonicity agent, a wetting agent, a thickening and viscosity agent, a density adjusting agent and combinations thereof.

In some preferred embodiments, the active lipid agent in the solid non-polar lipid particles is released from the solid non-polar lipid particles as individual molecules for a period of time after administration as an ophthalmic drop. In some preferred embodiments, the individual molecules are released for a period of from 1 up to 24 hours. In some preferred embodiments, the suspension is provided in a drop dispenser.

In some preferred embodiments, the present invention provides methods of treating a disease or disorder of the eye selected from the group consisting of evaporative dry eye, meibomian gland dysfunction and symptoms, clinical signs or conditions associated therewith, an unstable tear film resulting in rapid aqueous tear evaporation and keratoconjunctivitis sicca (dry eye) and symptoms or clinical signs associated therewith, in an animal or human subject in need of such treatment, comprising topically administering a lipid particle composition as described above comprising an effective amount of the active lipid agent to the eye of the subject. In some preferred embodiments, the subject in need of treatment has a tear film breakup time less than the normal clinical range of TBUT (tear break-up time) for the normal healthy population, e.g., in the United States or another country. In some preferred embodiments, the methods provide improvement (e.g., as compared to a control or reported by the patient) in one or more symptoms or measures selected from the group consisting of TBUT, eye comfort, eye dryness, vital conjunctival or corneal staining and Schirmer tear tests).

In some preferred embodiments, the present invention provides a lipid particle composition as described above for use in treating a disease or disorder of the eye selected from the group consisting of dry eye, inflammatory dry eye, evaporative dry eye, meibomian gland dysfunction and symptoms, clinical signs or conditions associated therewith, an unstable tear film resulting in rapid aqueous tear evaporation and keratoconjunctivitis sicca (dry eye) and symptoms or clinical signs associated therewith, in an animal or human subject in need of such treatment. In some preferred embodiments, administration of the compositions results in improvement (e.g., as compared to a control or reported by the patient) in one or more symptoms or measures selected from the group consisting of TBUT, eye comfort, eye dryness, vital conjunctival or corneal staining and Schirmer tear tests).

In a second aspect, the present invention provides drug delivery vehicles comprising solid non-polar lipid particles having an average particle size of less than 100 microns, and preferable less than 50 microns, the particles comprising an active agent (which can be denominated a second active agent where the lipids in the particle, for example the ether lipids described herein are denominated the first active agent) other than the lipids forming the solid non-polar lipid particles.

In some preferred embodiments, the solid non-polar lipid particles have a melting point of less than 80 degrees C. In some preferred embodiments, the solid non-polar lipid particles have a melting point of from 20 to 80 degrees C. In some preferred embodiments, the solid non-polar lipid particles have a melting point of from 30 to 60 degrees C. In some preferred embodiments, the solid non-polar lipid particles have an average particle size of less than 20 microns. In some preferred embodiments, the solid non-polar lipid particles have an average particle size of less than 10 microns.

In other preferred embodiments, the solid non-polar lipid particles comprise an ether lipid selected from the group consisting of:

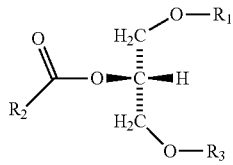

wherein
  $R_1$ is an unsubstituted C6 to C30 alkyl or alkenyl;
  $R_2$ is an unsubstituted C5 to C29 alkyl or alkenyl; and
  $R_3$ is a hydrogen (i.e., H);

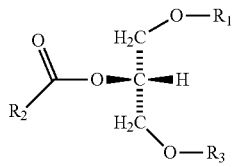

wherein
  $R_1$ is a hydrogen (i.e., H);
  $R_2$ is an unsubstituted C5 to C29 alkyl or alkenyl; and
  $R_3$ is an unsubstituted C6 to C30 alkyl or alkenyl; and

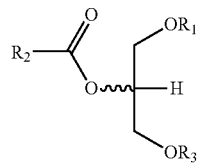

wherein
  $R_1$ is an unsubstituted C6 to C30 alkyl or alkenyl;
  $R_2$ is an unsubstituted C5 to C29 alkyl or alkenyl; and
  $R_3$ is a hydrogen (i.e., H).

In some preferred embodiments, the solid non-polar lipid particles comprise an ether lipid selected from the group consisting of:

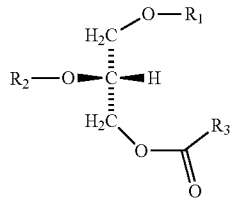

wherein
  $R_1$ is an unsubstituted C6 to C30 alkyl or alkenyl;
  $R_2$ is a hydrogen (i.e., H); and
  $R_3$ is an unsubstituted C5 to C29 alkyl or alkenyl;

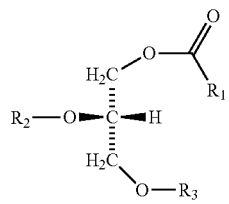

wherein
  $R_1$ is an unsubstituted C5 to C29 alkyl or alkenyl;
  $R_2$ is a hydrogen (i.e., H); and
  $R_3$ is an unsubstituted C6 to C30 alkyl or alkenyl; and

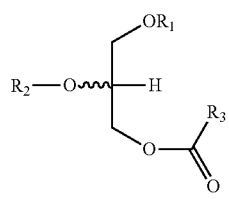

wherein
  $R_1$ is an unsubstituted C6 to C30 alkyl or alkenyl;
  $R_2$ is a hydrogen (i.e., H); and
  $R_3$ is an unsubstituted C5 to C29 alkyl or alkenyl.

In some preferred embodiments, the solid non-polar lipid particles comprise an ether lipid selected from the group consisting of 1-O-eicosanyl-2-palmitoyl-rac-glycerol (1,2-EPRG), sn-1-O-eicosanyl-2-palmitoyl-glycerol, sn-2-palmitoyl-3-O-eicosanyl-glycerol, 1-O-eicosanyl-3-palmitoyl-rac-glycerol (1,3-EPRG), sn-1-O-eicosanyl-3-palmitoyl-glycerol, sn-1-palmitoyl-3-O-eicosanyl-glycerol and mixtures thereof. In some preferred embodiments, the solid non-polar lipid particles comprise an ether lipid selected from the group consisting of 1-O-eicosanyl-2-palmitoyl-rac-glycerol (1,2-EPRG) or 1-O-eicosanyl-3-palmitoyl-rac-glycerol (1,3-EPRG) and mixtures thereof.

In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) and mixtures thereof is characterized in comprising greater than 95% (mole percent) of the 1-O-eicosanyl-2-palmitoyl-rac-glycerol (1,2-EPRG) isomer or greater than 95% (mole percent) of the 1-O-eicosanyl-3-palmitoyl-rac-glycerol (1,3-EPRG)isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer or greater than 98% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer or greater than 99% (mole percent) of the 1-O-eicosanyl-3-palmitoyl-rac-glycerol (1,3-EPRG) isomer.

In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 95%

(mole percent) of the 1-O-eicosanyl-2-palmitoyl-rac-glycerol (1,2-EPRG) isomer and no greater than 5% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer and no greater than 2% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer and no greater than 1% (mole percent) of the 1-O-eicosanyl-3-palmitoyl-rac-glycerol (1,3-EPRG) isomer.

In some preferred embodiments, the solid non-polar lipid particles further comprise one or more additional lipids selected from the group consisting of a nonpolar mono-, di- or tri-glyceride, a wax ester including cholesterol esters, a sterol, a free fatty acid and combinations thereof.

In some preferred embodiments, the active agent is selected from the group consisting of over the counter (OTC) or prescription topical ophthalmics, OTC or prescription topical ophthalmics for the treatment of dry eye, NMDA antagonists, anti-bacterials, antihistamines, decongestants, anti-inflammatories, antiparasitics, miotics, sympathomimetics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics, adrenergic anesthetics, beta blockers, alpha-2-agonists, cycloplegics, prostaglandins and combinations thereof.

In some preferred embodiments, the solid non-polar lipid particles are formulated as an aqueous suspension in a physiologically acceptable carrier. In some preferred embodiments, the liquid composition is a suspension of the solid micronized lipid particles in water containing phosphate buffered saline (PBS), 3% or less (w/w of the vehicle) polysorbate 80 and 0.3% or less (w/w of the vehicle) xanthan gum and has a pH of from 6.5-8.0 and an osmolality of from 260 to 320 mOsm/L.

In some preferred embodiments, the suspension is stable to phase separation of the solid non-polar lipid particles in the suspension for 6 months at room temperature. In some preferred embodiments, the suspension is chemically stable to <5% isomerization of 1,2-EPRG to the isomeric 1,3-EPRG during storage at room temperature for 6 months. In some preferred embodiments, the suspension is stable to phase separation of the solid non-polar lipid particles in the suspension for 24 months at room temperature. In some preferred embodiments, the suspension is chemically stable to <5% isomerization of 1,2-EPRG to the isomeric 1,3-EPRG during storage at room temperature for 24 months.

In some preferred embodiments, the suspension is sterile. In some preferred embodiments, the suspension comprises a preservative. In some preferred embodiments, the suspension is preservative-free. In some preferred embodiments, the physiologically acceptable carrier is an ophthalmologically acceptable carrier. In some preferred embodiments, the ophthalmologically acceptable carrier comprises an agent selected from the group consisting of a buffering agent, a tonicity agent, a wetting agent, a thickening and viscosity agent, a density adjusting agent and combinations thereof.

In some preferred embodiments, the active agent is released from the solid non-polar lipid particles as individual molecules of the active agent for a period of time after administration as an ophthalmic drop. In some preferred embodiments, the individual molecules are released for a period of from 1 up to 24 hours.

In some preferred embodiments, the suspension is provided in a drop dispenser.

In some preferred embodiments, the drug delivery vehicle is a medical insert device. In some preferred embodiments, the medical insert device is formed from a physiologically acceptable material. In some preferred embodiments, the physiologically acceptable material is a polymer. In some preferred embodiments, the physiologically acceptable material is selected from the group consisting of hydroxypropyl cellulose, a hydrogel, polymethyl methacrylate, and silicone acrylate. In some preferred embodiments, the medical insert device is selected from the group consisting of a punctal plug, a contact lens, and an ophthalmic insert. In some preferred embodiments, the medical insert device is rechargeable. In some preferred embodiments, the medical insert device is single use. In some preferred embodiments, the medical insert device is compatible with a mucosal surface. In some preferred embodiments, the mucosal surface is selected from the group consisting of an ocular mucosal surface, a vaginal mucosal surface, a nasal mucosal surface, an oropharyngeal mucosal surface, an oral cavity mucosal surface, and a rectal mucosal surface.

In some preferred embodiments, the present invention provides methods of delivering an active agent to a subject in need thereof comprising topically administering the drug delivery vehicle as described above to a subject. In some preferred embodiments, the drug delivery vehicle is administered to a mucosal surface of the subject. In some preferred embodiments, the mucosal surface is selected from the group consisting of an ocular mucosal surface, a vaginal mucosal surface, an oviduct mucosal surface, a respiratory system mucosal surface, a nasal mucosal surface, an oropharyngeal mucosal surface, an oral cavity mucosal surface, a rectal mucosal surface, a digestive system mucosal surface, and an esophageal mucosal surface. In some preferred embodiments, the drug delivery vehicle is applied or implanted under the mucosal surface. In some preferred embodiments, the mucosal surface is an ocular mucosal surface and the drug delivery vehicle is implanted or applied under the conjunctival or tenons capsule. In some preferred embodiments, the drug delivery vehicle is applied to an ocular mucosal surface by a route of delivery selected from the group consisting of retrobulbar, intracameral, intravitreal, suprachoroidal and subretinal routes of delivery.

In some preferred embodiments, the present invention provides methods of treating a disease or disorder of the eye selected from the group consisting of evaporative dry eye, meibomian gland dysfunction and symptoms, clinical signs or conditions associated therewith, an unstable tear film resulting in rapid aqueous tear evaporation and keratoconjunctivitis sicca (dry eye) and symptoms or clinical signs associated therewith, in an animal or human subject in need of such treatment, comprising topically administering a drug delivery vehicle as described above comprising an effective amount of the active lipid agent to the eye of the subject. In some preferred embodiments, the subject in need of treatment has a tear film breakup time less than the normal clinical range of TBUT (tear break-up time) for the normal healthy population, e.g., in the United States or another country. In some preferred embodiments, the methods provide improvement (e.g., as compared to a control or reported by the patient) in one or more symptoms or measures selected from the group consisting of TBUT, eye comfort, eye dryness, vital conjunctival or corneal staining and Schirmer tear tests).

In some preferred embodiments, the present invention provides a drug delivery vehicle as described above for use in treating a disease or disorder of the eye selected from the group consisting of dry eye, inflammatory dry eye, evaporative dry eye, meibomian gland dysfunction and symptoms, clinical signs or conditions associated therewith, an unstable tear film resulting in rapid aqueous tear evaporation and keratoconjunctivitis sicca (dry eye) and symptoms or clinical signs associated therewith, in an animal or human subject in need of such treatment. In some preferred embodiments, administration of the compositions results in improvement (e.g., as compared to a control or reported by the patient) in one or more symptoms or measures selected from the group consisting of TBUT, eye comfort, eye dryness, vital conjunctival or corneal staining and Schirmer tear tests).

In still other preferred embodiments, the present invention provides a lipid particle composition or drug delivery vehicle as described above for use in treating an animal or human subject in need of such treatment can be identified with a tear film breakup time (TBUT) below the clinically recognized normal range in that animal species or humans.

In a third aspect, the present invention provides a lipid particle composition comprising solid non-polar lipid particles comprising an active lipid agent and having an average particle size of less than 50 microns.

In some preferred embodiments, the solid non-polar lipid particles have a melting point of less than 80 degrees C. In some preferred embodiments, the solid non-polar lipid particles have a melting point of from 20 to 80 degrees C. In some preferred embodiments, the solid non-polar lipid particles have a melting point of from 30 to 60 degrees C. In some preferred embodiments, the solid non-polar lipid particles have an average particle size of less than 20 microns. In some preferred embodiments, the solid non-polar lipid particles have an average particle size of less than 10 microns.

In some preferred embodiments, the active lipid agent is a non-polar ether lipid.

In some preferred embodiments, the solid non-polar lipid particles comprise an active lipid agent selected from the group consisting of:

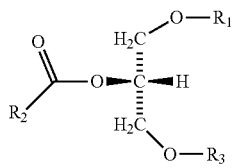

wherein
$R_1$ is an unsubstituted C6 to C30 alkyl or alkenyl;
$R_2$ is an unsubstituted C5 to C29 alkyl or alkenyl; and
$R_3$ is a hydrogen (i.e., H);

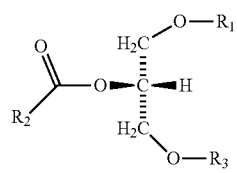

wherein
$R_1$ is a hydrogen (i.e., H);
$R_2$ is an unsubstituted C5 to C29 alkyl or alkenyl; and
$R_3$ is an unsubstituted C6 to C30 alkyl or alkenyl; and

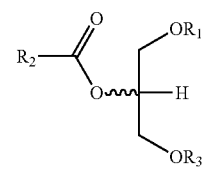

wherein
$R_1$ is an unsubstituted C6 to C30 alkyl or alkenyl;
$R_2$ is an unsubstituted C5 to C29 alkyl or alkenyl; and
$R_3$ is a hydrogen (i.e., H).

In some preferred embodiments, the solid non-polar lipid particles comprise an active lipid agent selected from the group consisting of:

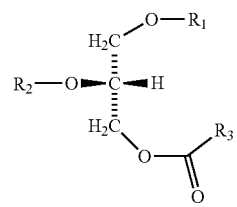

wherein
$R_1$ is an unsubstituted C6 to C30 alkyl or alkenyl;
$R_2$ is a hydrogen (i.e., H); and
$R_3$ is an unsubstituted C5 to C29 alkyl or alkenyl;

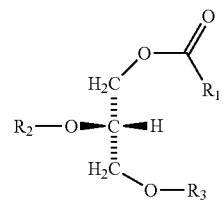

wherein
$R_1$ is an unsubstituted C5 to C29 alkyl or alkenyl;
$R_2$ is a hydrogen (i.e., H); and
$R_3$ is an unsubstituted C6 to C30 alkyl or alkenyl; and

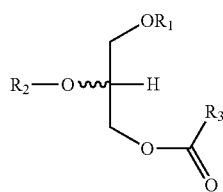

wherein
  $R_1$ is an unsubstituted C6 to C30 alkyl or alkenyl;
  $R_2$ is a hydrogen (i.e., H); and
  $R_3$ is an unsubstituted C5 to C29 alkyl or alkenyl.

In some preferred embodiments, the solid non-polar lipid particles comprise an active lipid agent selected from the group consisting of 1-O-eicosanyl-2-palmitoyl-rac-glycerol (1,2-EPRG), sn-1-O-eicosanyl-2-palmitoyl-glycerol, sn-2-palmitoyl-3-O-eicosanyl-glycerol, 1-O-eicosanyl-3-palmitoyl-rac-glycerol (1,3-EPRG), sn-1-O-eicosanyl-3 -palmitoyl-glycerol, sn-1-palmitoyl-3-O-eicosanyl-glycerol and mixtures thereof. In some preferred embodiments, the solid non-polar lipid particles comprise an active lipid agent selected from the group consisting of 1-O-eicosanyl-2-palmitoyl-rac-glycerol (1,2-EPRG) or 1-O-eicosanyl-3-palmitoyl-rac-glycerol (1,3-EPRG) and mixtures thereof.

In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 95% (mole percent) of the 1-O-eicosanyl-2-palmitoyl-rac-glycerol (1,2-EPRG) isomer or greater than 95% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer or greater than 98% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer or greater than 99% (mole percent) of the 1-O-eicosanyl-3-palmitoyl-rac-glycerol (1,3-EPRG) isomer.

In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 95% (mole percent) of the 1-O-eicosanyl-2-palmitoyl-rac-glycerol (1,2-EPRG) isomer and no greater than 5% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer and no greater than 2% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer and no greater than 1% (mole percent) of the 1-O-eicosanyl-3-palmitoyl-rac-glycerol (1,3-EPRG) isomer.

In some preferred embodiments, the solid non-polar lipid particles further comprise one or more additional lipids selected from the group consisting of a nonpolar mono-, di- or tri-glyceride, a wax ester including cholesterol esters, a sterol, a free fatty acid and combinations thereof.

In some preferred embodiments, the solid non-polar lipid particles are formulated as a suspension.

In some preferred embodiments, the solid non-polar lipid particles are provided as a medical insert device. In some preferred embodiments, the medical insert device is formed from a physiologically acceptable material. In some preferred embodiments, the physiologically acceptable material is a polymer. In some preferred embodiments, the physiologically acceptable material is selected from the group consisting of hydroxypropyl cellulose, a hydrogel, polymethyl methacrylate, and silicone acrylate. In some preferred embodiments, the medical insert device is selected from the group consisting of a punctal plug, a contact lens, and an ophthalmic insert. In some preferred embodiments, the medical insert device is rechargeable. In some preferred embodiments, the medical insert device is single use. In some preferred embodiments, the medical insert device is compatible with a mucosal surface. In some preferred embodiments, the mucosal surface is selected from the group consisting of an ocular mucosal surface, a vaginal mucosal surface, a nasal mucosal surface, an oropharyngeal mucosal surface, an oral cavity mucosal surface, and a rectal mucosal surface.

In some preferred embodiments, the lipid particle may preferably comprise a second active agent in addition to the first active agent (i.e., the ether lipid). In some preferred embodiments, the active agent is selected from the group consisting of over the counter (OTC) or prescription topical ophthalmics, OTC or prescription topical ophthalmics for the treatment of dry eye, NMDA antagonists, anti-bacterials, antihistamines, decongestants, anti-inflammatories, anti-parasitics, miotics, sympathomimetics, anticholinergics, adrenergics, antivirals, local anesthetics, antifungals, amoebicidals, trichomonocidals, analgesics, mydriatics, antiglaucoma drugs, carbonic anhydrase inhibitors, ophthalmic diagnostic agents, ophthalmic agents used as adjuvants in surgery, chelating agents, antineoplastics, antihypertensives, muscle relaxants, diagnostics, adrenergic anesthetics, beta blockers, alpha-2-agonists, cycloplegics, prostaglandins and combinations thereof.

In some preferred embodiments, the present invention provides methods of treating a disease or disorder associated with a mucous membrane comprising administering a lipid particle composition as described above to a subject in need thereof. In some preferred embodiments, the disease or disorder is a disease or disorder of the eye selected from the group consisting of dry eye, inflammatory dry eye, evaporative dry eye, meibomian gland dysfunction and symptoms, clinical signs or conditions associated therewith, an unstable tear film resulting in rapid aqueous tear evaporation and keratoconjunctivitis sicca (dry eye) and symptoms or clinical signs associated therewith, in an animal or human subject in need of such treatment. In some preferred embodiments, administration of the compositions results in improvement (e.g., as compared to a control or reported by the patient) in one or more symptoms or measures selected from the group consisting of TBUT, eye comfort, eye dryness, vital conjunctival or corneal staining and Schirmer tear tests).

In some preferred embodiments, the present invention provides for use of a lipid particle composition as described above to treat a disease or disorder of the mucous membrane of a subject. In some preferred embodiments, the disease or disorder is a disease or disorder of the eye selected from the group consisting of dry eye, inflammatory dry eye, evaporative dry eye, meibomian gland dysfunction and symptoms, clinical signs or conditions associated therewith, an unstable tear film resulting in rapid aqueous tear evaporation and keratoconjunctivitis sicca (dry eye) and symptoms or clinical signs associated therewith, in an animal or human subject in need of such treatment. In some preferred embodiments, administration of the compositions results in improvement (e.g., as compared to a control or reported by the patient) in one or more symptoms or measures selected from the group consisting of TBUT, eye comfort, eye dryness, vital conjunctival or corneal staining and Schirmer tear tests).

BRIEF DESCRIPTION OF THE DRAWINGS

FIG. 3 is a photograph of stably suspended solid micronized particles in the presence of different concentrations of xanthan gum excipient.

FIG. 6 provides graphs that demonstrate that administration of the micronized solid lipid particles of the present invention brought about an extension in TBUT in five healthy dogs after a single administration.

DEFINITIONS

Figure 1:
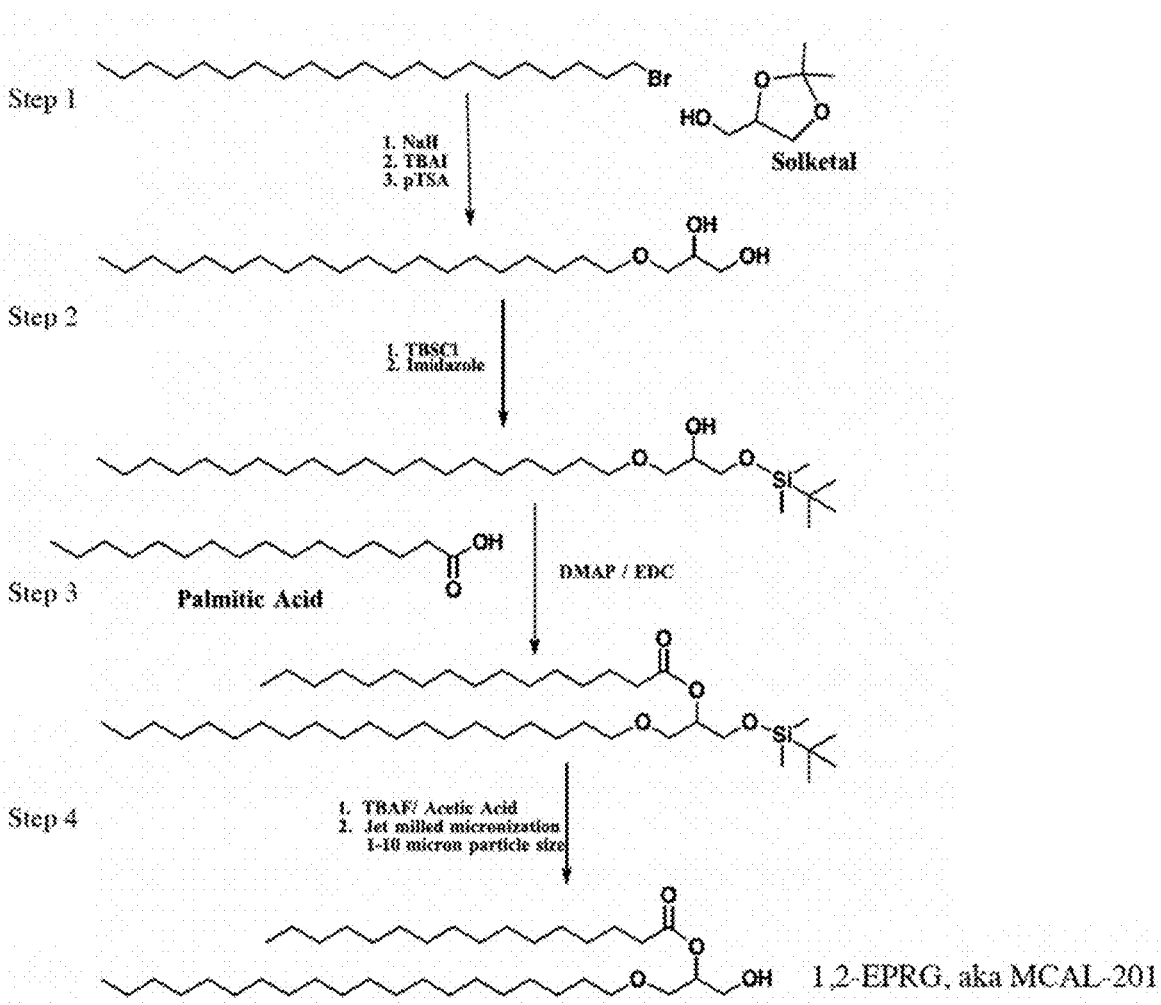
FIG. 1 is schematic drawing for the synthesis of lipids used in embodiments of the present invention.

A "patient," "subject," or "individual" are used interchangeably and refer to either a human or a non-human animal. These terms include mammals, such as humans, primates, livestock animals (including bovines, swine, etc.), companion animals (e.g., canines, felines, etc.) and rodents (e.g., mice and rats). "Administering" or "administration of" a substance, a compound or an agent to a subject can be carried out using one of a variety of methods known to those skilled in the art. For example, a compound or an agent can be administered, topically, ophthalmically, intravenously, arterially, intradermally, intra-muscularly, intraperitonealy, intravenously, subcutaneously, sublingually, orally (by ingestion), intranasally (by inhalation), intraspinally, intracerebrally, and transdermally (by absorption, e.g., through a skin duct). Specific ocular administration routes include topical administration to the ocular surface (cornea and/or conjunctiva), subconjunctival administration, sub tenon's capsule administration, retrobulbar administration, intracameral administration, intravitreal administration, suprachoroidal administration and sub-retinal administration. A compound or agent can also appropriately be introduced by rechargeable or biodegradable polymeric devices or other devices, e.g., patches and pumps, or formulations, which provide for the extended, slow or controlled release of the compound or agent. The polymeric materials may be solid implantable materials or may be designed such as to maintain prolonged contact with the ocular surface (a commercial example is LACRISER™, see world wide web at bausch.com/ecp/our-products/ rx-pharmaceuticals/rx-pharmaceuticals/lacrisert) or be formed or included into punctal plugs that slowly release the test article (e.g., see the world wide web at ois.net/punctal-plugs-for-sustained-delivery/) or O rings that are placed into the conjunctival fornices (e.g. https://www.aao.org/eye-health/news/new-glaucoma-treatment-ring-shows-promise). Other embodiments as to therapeutic constructs are exemplified but not limited to materials applied topically or injected into and/or around the eye that form hydrogels whose polymerization is triggered by changes in temperature, pH or ionic composition. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

An "active lipid agent" is a lipid that has therapeutic effect on mucosal surfaces. The solid crystalline or amorphous active lipid agent can also act as a slow release delivery vehicle for monomeric molecules of the active lipid agent when micronized and suspended in a buffer whose tonicity, viscosity and density are adjusted to support a stable suspension of the micronized solid active lipid agent.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations on a one time, multi dose, daily, weekly or other therapeutic timeframe. The precise effective amount needed for a subject will depend upon, for example, the subject's size, health and age, the nature and extent of the condition being treated, such as dry eye and/or other eye disorder. The skilled worker can readily determine the effective amount for a given situation by routine experimentation.

As used herein, the term "shelf life" means the time period from the date of manufacture of the product until a drug is administered.

"Treating" a condition or patient refers to taking steps to obtain beneficial or desired results, including clinical results. Beneficial or desired clinical results include, but are not limited to, alleviation, amelioration, or slowing the progression, of one or more symptoms associated with mucosal surface deficiencies, particularly lipid deficiencies, as well as with a neuronal disorder, including neurodegeneration and traumatic brain injury, as well as pain and discomfort. In certain embodiments, treatment may be prophylactic. Exemplary beneficial clinical results are described herein.

As used herein, the term chemical formula includes information about the spatial arrangement of atoms and bonds in a chemical but not necessarily the exact isomer, analog or homolog; while the term molecular formula refers to the number of atoms of each element in the compound.

"Alkyl" refers to a monovalent straight-chain, branched or cyclic saturated aliphatic hydrocarbon radical. Preferably, the alkyl group is a straight chain radical having 1 to 40 carbon atoms. More preferably, it is an alkyl radical of from 5 to 31 carbon atoms, most preferably 15 to 23 carbon atoms. Typical alkyl radicals include pentyl, hexyl, tridecanyl, tetradecanyl, nonadecanyl, docosanyl, triacontanyl, hentriacontanyl and the like. Preferably this term denotes an acyclic carbon or a saturated acyclic carbon chain represented by the formula CnH2n+1 wherein n is an integer of from 1 to 31.

"Alkenyl" refers to a monovalent, straight-chain, branched or cyclic, unsaturated aliphatic hydrocarbon radical having one or more, preferably one, double bond. Preferably, the alkenyl radical has from 2 to 40 carbon atoms. More preferably, it is an alkenyl radical of from 6 to 30 carbon atoms, most preferably 15 to 23 carbon atoms. Typical alkenyl groups include hexenyl, tridecenyl, tetradecenyl, nonadecenyl, docosenyl, triacontenyl, hentriacontenyl and the like. Preferably this term denotes an acyclic carbon chain which contains a carbon-to-carbon double bond and is represented by the formula CnH2n-1 wherein n is an integer of from 2 to 40. Preferably the geometry of the alkenyl bond is of the cis or Z-configuration commonly found in cellular membrane lipids.

"Alkylene" refers to a divalent, straight-chain, branched or cyclic, saturated aliphatic hydrocarbon radical. Preferably, the alkylene group has from 1 to 12 carbon atoms. This term denotes an acyclic carbon or a saturated acyclic carbon chain represented by the formula CnH2n-2 wherein n is an integer of from 1 to 12. More preferably, it is a lower alkylene of from 1 to 7 carbon atoms, most preferably from 1 to 4 carbon atoms, e.g., methylene.

The term "aliphatic" as used herein means a straight chained or branched alkyl, alkenyl or alkynyl. It is understood that alkenyl or alkynyl embodiments need at least two carbon atoms in the aliphatic chain. Aliphatic groups typically contains from 1 (or 2) to 30 carbons, such as from 1 (or 2) to 20 carbons.

As used herein, the carbon atom designations may have the indicated integer and any intervening integer. For example, the number of carbon atoms in a (C1-C4)-alkyl group is 1, 2, 3, or 4. It should be understood that these designations refer to the total number of atoms in the appropriate group.

"Pharmaceutically acceptable salt" or "salt" is used herein to refer to an agent or a compound according to the disclosure that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like.

DETAILED DESCRIPTION

The present invention relates to drug delivery vehicles comprising micronized crystalline or amorphous solid that include an active lipid agent, and in particular to crystalline or amorphous solid micronized lipid particles that comprise an ether lipid such as sn-1-O-eicosanyl-sn-2-palmitoyl-glycerol and its isomers.

The disclosure contemplates that any one or more of the foregoing aspects and embodiments can be combined with each other and/or with any of the embodiments or features provided below.

Mucous membranes have epithelial constituents that possess an intrinsic surface chemistry and the most superficial layer of cells have nano through micron scale topographic features in the form of microvilli and microplicae. The topographic features interact with the thin fluid films in intimate association with the cellular constituents and likely contribute to the relative stability of the thin films. It is known that these surface topographic features can be altered in disease states of the ocular surface and such alterations may contribute to thin film instability. Thin films of fluids, including but not limited to tears, saliva, gastrointestinal coatings, thin films associated with the eyelid, the ocular surface and pen-ocular tissue, the respiratory tract (nasal passages, trachea, bronchi, bronchioles and alveoli) and cervico-vaginal secretions and thin films associated with the rest of the female reproductive tract, cover the cellular elements of mucous membranes in all vertebrate species. Tatematsu et al., Bone Marrow Transplant. 2012 Mar.;47(3):416-25. doi: 10.1038/bmt.2011.89. Epub 2011 May 16.

The secretions covering mucous membranes come from a variety of sources, and have three broad classes of constituents. The glycosaminoglycan (or mucous) layer; aqueous components containing soluble species such as proteins, sugars, salts and osmolytes; and in the case of tears, a lipid-containing component. The mucous membrane thin films come from cells embedded in the mucous membranes (or proximal to the mucous membranes) or from glandular structures. Water forms the basis of lubrication in the human body, particularly at water interfaces with lipids, waxes and oils, but may be unable to provide sufficient lubrication without additives in diseased states. The importance of biolubrication becomes evident upon aging and disease, particularly under conditions that affect secretion or composition of body fluids. Insufficient biolubrication, may impede proper speech, mastication and swallowing, underlie excessive friction and wear of articulating cartilage surfaces in hips and knees, cause vaginal dryness, and result in dry, irritated eyes. The act of blinking an average of 28,800 times per day may represent the most frequently used frictional surface interaction. The average time between blinks can be measured and may be limited by the integrity of the tear film and tear film lipid layer. Insufficient biolubrication of the ocular surface and eyelids leads to more frequent and high friction blinking and irritation. Over time, this leads to the inflammation behind dry eye. Clinical improvement in biolubrication of the ocular surface can be measured as longer interblink times, slower blinking, fewer blink per minute, hour or day, improved patient comfort and increases in the tear film breakup time (TBUT). Biolubrication is due to a combination of structure, lipid layers and glycosylation of adsorbed protein films, providing an important clue to design effective therapeutics to restore biolubrication in patients with insufficient biolubrication. Veeregowda et al., PLoS One. 2012;7(8):e42600. doi: 10.1371/journal.pone.0042600. Epub 2012 Aug. 15.

As a non-limiting example, a widely accepted model of the tear film that coats the ocular surface is one that is comprised of three major constituents; an outer lipid layer derived from glands that line the lid margin (Meibomian or tarsal glands as well as secretions from Harderian glands in species that possess one including the rabbit); an aqueous layer derived from lacrimal and accessory lacrimal glands (with admixed soluble proteins as well as admixed lipids and mucins); and a mucin layer derived from goblet cells associated with the conjunctival and corneal epithelial cells as well as mucins that originate from the epithelial cells themselves.

The mucin constituents form a layer immediately adjacent to the cellular elements of the ocular surface such as the corneal epithelium and are thought to associate to a degree with the glycocalyx of the most superficial epithelial cells, as well as being admixed in the thicker aqueous component. The mucin elements are thought to be important for maintaining the stability of the tear film by affecting the surface tension of the cellular aqueous layer interface. The aqueous layer is the largest component of the tear film and contains a variety of solutes for maintaining tear pH, osmolality and ocular health. Immunoglobulins, lysozyme, transferrin, antimicrobial peptides and other constituents assist in controlling bioburden and decreasing the risk of infection. Mucins can also be admixed within this layer. Additionally, growth factors, cytokines and other cytoactive factors are found within the aqueous layer. The polar lipids of the tear film lipid layer coats the aqueous layer with a monomolecular layer of lipid molecules with charged head groups oriented toward the aqueous layer. The outer tear film non-polar lipid layer is the outermost layer of the tear film and is directly in contact with air. This non-polar lipid layer provides lubrication as well as stability to the overall tear film as measured clinically as the tear breakup time and decreases rates of evaporation of the aqueous component of the tear film.

A number of diseases and conditions are associated with dry or dysfunctional mucous membranes. These are exemplified by, but not limited to, dry eye, dry mouth, vaginal drying and diseases involving deficiencies/dysregulation in respiratory thin film coatings. What is needed are safe, effective, and flexible means for treating dry or dysfunctional mucous membrane diseases as well as therapies aimed at improving the performance of non-diseased mucous membranes.

A broad challenge to the development of effective therapeutic agents is the formulation and delivery of hydrophobic molecules to the therapeutic benefit of mucosal surfaces as well as delivery of therapeutics that must cross intact mucosal surfaces to have a therapeutic benefit to deeper lying tissues/structures. The novelty and practicality of the invention described herein is the integration of highly hydrophobic molecules as low temperature melting crystalline and amorphous lipids and waxes or as molecules embedded in low melting crystalline and amorphous solid lipids and waxes that can be suspended as small particulates or dissolved within a formulation for topical application from a biocompatible water based formulation in which the lipids are inherently insoluble and/or be integrated into devices for controlled release of therapeutically beneficial compounds from a low melting crystalline and amorphous solid or wax. Additionally, it is contemplated that these low temperature melting crystalline and amorphous solid lipids and waxes provide a means of controlled delivery for hydrophilic or amphiphilic compounds trapped within low temperature melting lipids and waxes. For example, in the case of drug delivery vehicles comprising micronized solid particles that include an active lipid agent, and in particular to micronized lipid particles that comprise an ether lipid such as sn-1-O-eicosanyl-sn-2-palmitoyl-glycerol and its isomers with a second active ophthalmic agent such as cyclosporin or Xiidra for the treatment of dry eye including inflammatory and/or evaporative dry eye. Micronized crystalline or amorphous solid lipid particles that comprise an ether lipid such as sn-1-O-eicosanyl-sn-2-palmitoyl-glycerol can be prepared by spray drying from a 40 mg/mL solution of the ether lipid in chloroform into a vacuum chamber. This results in micronized amorphous solid lipid particles of less than 10 microns. Addition of a second active agent (e.g., cyclosporin, Xiidra or any of the second active agents described below) into the chloroform solution for spray drying can result in spray dried micronized lipid particles containing therapeutic amounts of both the ether lipid and second active agent. Alternatively, nano-sized particulate solid suspensions of second active agents in amorphous 1,2 EPRG may be formed by spray dry micronization of a solution of 1,2-EPRG in chloroform or other suitable solvent containing suspended nano-ized particles of the second active agent.

In certain aspects, the drug delivery vehicles as described herein can be used to treat patients suffering from disorders of the mucosal membrane. The drug delivery vehicles of the present invention further find use where delivery of an active lipid agent or lipophilic drug to the mucosal membrane is desired as a route of administration. As such, the present invention provides drug delivery vehicles that are useful for delivery an active lipid component or other lipophilic drug to the mucous membrane of subject. The present invention is not limited to any particular mucosal surface. In some preferred embodiments, the mucosal surface is ocular mucosal surface, a vaginal mucosal surface, an oviduct mucosal surface, a respiratory system mucosal surface, a nasal mucosal surface, an oropharyngeal mucosal surface, an oral cavity mucosal surface, a rectal mucosal surface, a digestive system mucosal surface, or an esophageal mucosal surface. The present invention is not limited to any particular route of delivery. In some preferred embodiments, the route of delivery comprises topical administration. In some embodiments, where the target organ is the eye, preferred routes of delivery include topical ophthalmic drops, in addition to subconjunctival, sub-Tenon's capsule, retrobulbar, intracameral, intravitreal, suprachoroidal and subretinal routes of delivery.

In some preferred embodiments, the drug delivery vehicles of the present invention comprise crystalline and amorphous solid micronized lipid particles. In some preferred embodiments, the micronized lipid particles have an average size of less than 100 microns. In some more preferred embodiments, the crystalline and amorphous solid micronized lipid particles have an average size of less than 50 microns. In some more preferred embodiments, the crystalline and amorphous solid micronized lipid particles have an average size of less than 20 microns. In some still more preferred embodiments, the crystalline and amorphous solid micronized lipid particles have an average size of less than 10 microns. In some preferred embodiments, the crystalline and amorphous solid micronized lipid particles have an average size of from 1 to 100, 1 to 50, or 1 to 10 microns. In some preferred embodiments, the particle size is assayed by dynamic light scattering.

In some preferred embodiments, the micronized lipid particles of the present invention have a melting point of less than 80 degrees C. In some more preferred embodiments, the micronized lipid particles of the present invention have a melting point of less than 60 degrees C. In some still more preferred embodiments, the micronized lipid particles of the present invention have a melting point of less than 50 degrees C. In some other preferred embodiments, the solid micronized lipid particles have a melting point of from 20 to 80 degrees C. In still other preferred embodiments, the solid micronized lipid particles have a melting point of from 30 to 60 degrees C.

It will be understood that lipid composition of the micronized lipid particles may be varied to provide a desired melting point. Accordingly, in some preferred embodiments, the micronized lipid particles of the present invention comprise one or more carrier lipids such as monoglycerides, diglycerides, ether ester glycerol, triglycerides, phospholipids, waxes or sterols. In some embodiments, the lipids may comprise fatty acid moieties that are attached to a glycerol backbone by either ester or ether bonds.

A variety of methods for preparing micronized particles are known in the art. In some preferred embodiments, the micronized particles are prepared by jet milling. Suitable jet mills are available from, for example, Hosokawa Micron Powder Systems, Summit, NJ. Feed product, for example, a lipid composition of the present invention is fed into a grinding zone of the jet mill. Grinding air is injected tangentially via Laval nozzles in the nozzle ring into the jet mill. This causes a spiral jet of air to form in the grinding zone. A high pressure forms in the mill as a result of the spiral flow of air that can rise to 1 bar overpressure in operation without product. The integrated injector is charged with compressed air which ensures that the product is conveyed into the machine against the overpressure present in the machine.

The feed product circulates close to the nozzle ring and is thus intercepted repeatedly by the air jets exiting the nozzles. Comminution is the result of inter-particle collision caused by the particles flowing at different speeds in the nozzle jet. Comminuted material is conveyed along with the air to the discharge. The spiral flow subjects the particles to a classification where only fine (i.e., micronized) particles are discharged and coarse particles remain in the mill.

In some preferred embodiments, the micronized particles are prepared by spray drying a solution of lipid composition with or without a second active agent of the present invention is fed via a nozzle into a vacuum chamber where the solvent evaporates to yield amorphous solid 5 to 50 micron sized particles which settle and are collected. One such spray drying device is sold by Buchi instruments and described at this url: https://static1.buchi.com/sites/default/files/downloads/Spray_Drying_Encapsulation_Solutions_brochure_en_D_0.pdf?56fa5dfle4976c154c3b11af6a45ff69b22d63e3

In some preferred embodiments, micronized lipid particles comprise an active lipid agent. Active lipid agents are lipid molecules that confer a therapeutic or prophylactic benefit or treat a disease or condition. Active lipid agents of use in the present invention include but are not limited to monoglycerides, diglycerides, triglycerides, ether ester glycerol, phospholipids, waxes or sterols.

In some preferred embodiments, the active lipid agent is an ether lipid. Suitable ether lipids are described in detail in U.S. Pat. No. 9,289,494 which is incorporated herein by reference in its entirety.

Figure 7:
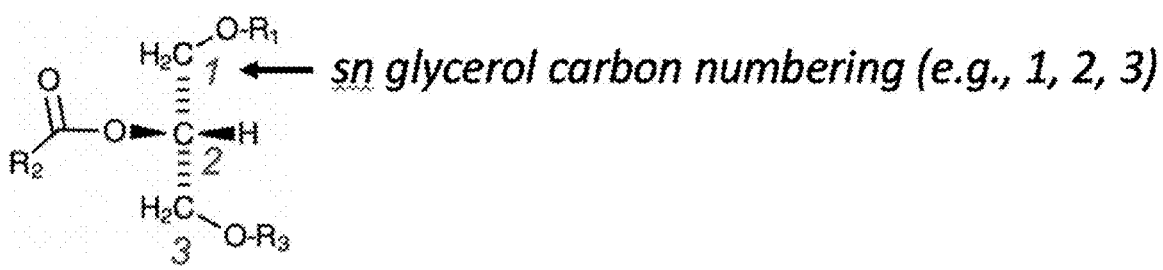
FIG. 7 provides an exemplary structure that identifies the sn- numbering of the carbons of a glycerol backbone.

In some preferred embodiments, the active lipid agent is a sn-1,2 substituted glycerol, sn-2,3 substituted glycerol, or 1,2-substituted racemic glycerols (i.e., 1,2-rac-glycerol), preferably comprising a fatty acid moiety attached to the glycerol via an ether linkage. The stereospecific numbering, sn- of the glycerol backbone carbons is shown in FIG. 7 for a 1,2-substituted ether lipid where, for example, $R_1$ is an alkyl or alkenyl attached via an ether linkage, $R_2$ is an alkyl or alkenyl attached via an ester linkage, and $R_3$ is a —H. This sn-numbering of the glycerol backbone carbons applies to the structures presented herein.

In some embodiments, the active lipid agent is an ether lipid selected from:

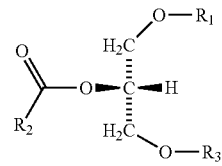

wherein
$R_1$ is an unsubstituted C6 to C30 alkyl or alkenyl, preferably a C20 alkyl or alkenyl;
$R_2$ is an unsubstituted C5 to C29 alkyl or alkenyl, preferably a C15 alkyl or alkenyl; and
$R_3$ is a hydrogen (i.e., H);

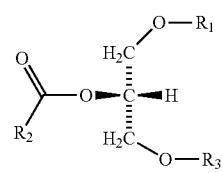

wherein
$R_1$ is a hydrogen (i.e., H);
$R_2$ is an unsubstituted C5 to C29 alkyl or alkenyl, preferably a C15 alkyl or alkenyl; and
$R_3$ is an unsubstituted C6 to C30 alkyl or alkenyl, preferably a C20 alkyl or alkenyl; and

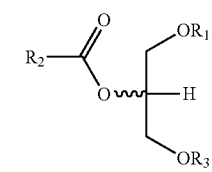

wherein
$R_1$ is an unsubstituted C6 to C30 alkyl or alkenyl, preferably a C20 alkyl or alkenyl;
$R_2$ is an unsubstituted C5 to C29 alkyl or alkenyl, preferably a C15 alkyl or alkenyl; and
$R_3$ is a hydrogen (i.e., H).

In some preferred embodiments, the active lipid agent is a sn-1,3 substituted glycerol or 1,3-substituted racemic glycerols (i.e., 1,3-rac-glycerol), preferably comprising a fatty acid moiety attached to the glycerol via an ether linkage, selected from:

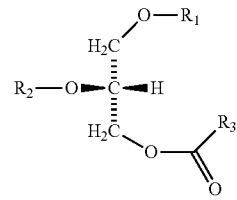

wherein
$R_1$ is an unsubstituted C6 to C30 alkyl or alkenyl, preferably a C20 alkyl or alkenyl;

$R_2$ is a hydrogen (i.e., H); and
$R_3$ is an unsubstituted C5 to C29, preferably a C15 alkyl or alkenyl alkyl or alkenyl;

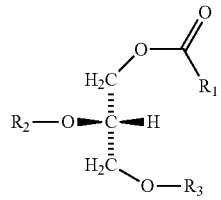

wherein
$R_1$ is an unsubstituted C5 to C29 alkyl or alkenyl, preferably a C15 alkyl or alkenyl;
$R_2$ is a hydrogen (i.e., H); and
$R_3$ is an unsubstituted C6 to C30 alkyl or alkenyl, preferably a C20 alkyl or alkenyl; and

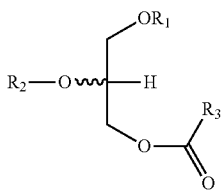

wherein
$R_1$ is an unsubstituted C6 to C30 alkyl or alkenyl, preferably a C20 alkyl or alkenyl;
$R_2$ is a hydrogen (i.e., H); and
$R_3$ is an unsubstituted C5 to C29 alkyl or alkenyl. preferably a C15 alkyl or alkenyl.

In some preferred embodiments, the active lipid agent is an ether ester glycerol lipid selected from the group consisting of 1-O-eicosanyl-2-palmitoyl-rac-glycerol (1,2-EPRG), sn-1-O-eicosanyl-2-palmitoyl-glycerol, sn-2-palmitoyl-3-O-eicosanyl-glycerol, 1-O-eicosanyl-3-palmitoyl-rac-glycerol (1,3-EPRG), sn-1-O-eicosanyl-3-palmitoyl-glycerol, sn-1-palmitoyl-3-O-eicosanyl-glycerol and mixtures thereof. In some further preferred embodiments, the active lipid agent is an ether lipid is selected from the group consisting of 1-O-eicosanyl-2-palmitoyl-rac-glycerol (1,2-EPRG) or 1-O-eicosanyl-3-palmitoyl-rac-glycerol (1,3-EPRG) and mixtures thereof.

Accordingly, in some preferred embodiments, one of the sn- positions of the lipid molecules of the present invention is an —OH group and the other of the two sn- positions have an ether-linked aliphatic chain and an ester-linked aliphatic chain so that the ether lipid is an ether ester glycerol. It will be understood that where the ether lipid comprises two aliphatic chains, isomeric forms are possible. For example, when the alkyl or alkenyl ether is attached to the glycerol backbone sn-1 position of diglyceride, the fatty acid attached to the glycerol backbone via an ester bond may be present at either sn-2 or sn-3 positions of the glycerol backbone. Likewise, when the fatty acid is attached to the glycerol backbone via an ester bond is present at the sn-1 position of diglyceride, the alkyl or alkenyl ether attached to the glycerol backbone may be present at either sn-2 or sn-3 positions of the glycerol backbone. In this regard, it will be apparent to one of skill in the art that when labelling the diglyceride molecule, the sn-1 and sn-3 positions will be dependent on orientation of the molecule. For example, sn-1-O-eicosanyl-sn-2-palmitoyl-glycerol and sn-3-O-eicosanyl-sn-2-palmitoyl-glycerol are isomers.

It will further be understood that when the active lipid agent is a ether ester glycerol, that the active lipid agent may be a mixture of isomeric forms of the disubstituted glycerol and that the mixture may be characterized by the mole percentage of the mixture of ether ester glycerol isomers.

Accordingly, in some preferred embodiments, the mixture of ether ester lipid isomers 1-O-eicosanyl-2-palmitoyl-rac-glycerol (1,2-EPRG) and 1-O-eicosanyl-3-palmitoyl-rac-glycerol (1,3-EPRG) and mixtures thereof is characterized in comprising greater than 95% (mole percent) of the 1-O-eicosanyl-2-palmitoyl-rac-glycerol (1,2-EPRG) isomer or greater than 95% (mole percent) of the 1-O-eicosanyl-3-palmitoyl-rac-glycerol (1,3-EPRG) isomer. In some preferred embodiments, the mixture of ether ester lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer or greater than 98% (mole percent) of the 1-O-eicosanyl-3-palmitoyl-rac-glycerol (1,3-EPRG) isomer. In some preferred embodiments, the mixture of ether ester lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer or greater than 99% (mole percent) of the 1-O-eicosanyl-3-palmitoyl-rac-glycerol (1,3-EPRG) isomer.

In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 50% (mole percent) of the 1-O-eicosanyl-2-palmitoyl-rac-glycerol (1,2-EPRG) isomer and no greater than 50% (mole percent) of the 1-O-eicosanyl-3-palmitoyl-rac-glycerol (1,3-EPRG) isomer. In some preferred embodiments, the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising no greater than 50% (mole percent) of the 1-O-eicosanyl-2-palmitoyl-rac-glycerol (1,2-EPRG) isomer and more than 50% (mole percent) of the 1-O-eicosanyl-3-palmitoyl-rac-glycerol (1,3-EPRG) isomer.

In some preferred embodiments, the mixture of ether ester lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 95% (mole percent) of the 1-O-eicosanyl-2-palmitoyl-rac-glycerol (1,2-EPRG) isomer and no greater than 5% (mole percent) of the 1-O-eicosanyl-3-palmitoyl-rac-glycerol (1,3-EPRG) isomer. In some preferred embodiments, the mixture of ether ester lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer and no greater than 2% (mole percent) of the 1-O-eicosanyl-3-palmitoyl-rac-glycerol (1,3-EPRG) isomer. In some preferred embodiments, the mixture of ether ester lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer and no greater than 1% (mole percent) of the 1-O-eicosanyl-3-palmitoyl-rac-glycerol (1,3-EPRG) isomer.

The crystalline or amorphous solid micronized lipid particles of the present invention may comprise other active agents such as hydrophilic, amphiphilic or lipophilic active agents. In some of these preferred embodiments, the active agent may be formulated with a carrier lipid, with a carrier lipid and an active lipid, or an active lipid.

Suitable active agents that are not active lipid agents include many different types of drug molecules. Suitable exemplary drug molecules are described below. It will be recognized by those skilled in the art that whole molecules, isomers, as well as fragments of compounds known to have activity represent acceptable compounds for inclusion.

Active agents suitable for inclusion in the drug delivery vehicles of the present invention include but are not limited to small molecule drugs, biologic agents such as proteins, RNA and DNA based therapeutic agents, and other molecules having a therapeutic or prophylactic benefit or which are used to treat a disease or condition. In some preferred embodiments, the agents are selected from an agent that stabilizes thin films that coat mucosal surfaces, a lubricating agent, agents that enhance the wetting of thin films coating mucosal surfaces (e.g., pluronics), an ophthalmic agent for the treatment of the ocular surface, an ophthalmic agent for the treatment of the pen-ocular tissue, an ophthalmic agent for the treatment of the posterior ocular tissue and diseases, an ophthalmic agent for the treatment of dry eye chosen from corticosteroids, cyclosporin, Xiidra or other active ingredients in FDA approved treatments for dry eye, an antimicrobial agent, an antiviral agent, a polypeptide antimicrobial agent, an antifungal agent, a buffering agent, a vitamin or mineral, an analgesic agent, an anticoagulant agent, a coagulating agent, an anti-inflammatory agent, a vasoconstrictor agent, a vasodilating agent, a diuretic agent, an anticancer agent, a trophic agent, a growth factor, a neurotrophic agent, a biofilm disrupting agent, an agent that affects intraocular pressure by affecting aqueous drainage and/or production, a promoter of neovascularization agent, an inhibitor of neovascularization agent, an extracellular matrix (ECM) agent, an enzyme agent, an enzyme inhibiting agent, and polypeptide agents and combinations thereof.

In some embodiments, an antimicrobial agent is incorporated into the solid lipid particles. Suitable antimicrobials include but are not limited to loracarbef, cephalexin, cefadroxil, cefixime, ceftibuten, cefprozil, cefpodoxime, cephradine, cefuroxime, cefaclor, neomycin/polymyxin/bacitracin, dicloxacillin, nitrofurantoin, nitrofurantoin macrocrystal, nitrofurantoin/nitrofuran mac, dirithromycin, gemifloxacin, ampicillin, gatifloxacin, penicillin V potassium, ciprofloxacin, enoxacin, amoxicillin, amoxicillin/clavulanate potassium, clarithromycin, levofloxacin, moxifloxacin, azithromycin, sparfloxacin, cefdinir, ofloxacin, trovafloxacin, lomefloxacin, methenamine, erythromycin, norfloxacin, clindamycin/benzoyl peroxide, quinupristin/dalfopristin, doxycycline, amikacin sulfate, vancomycin, kanamycin, netilmicin, streptomycin, tobramycin sulfate, gentamicin sulfate, tetracyclines, framycetin, minocycline, nalidixic acid, demeclocycline, trimethoprim, miconazole, colistimethate, piperacillin sodium/tazobactam sodium, paromomycin, colistin/neomycin/hydrocortisone, amebicides, sulfisoxazole, pentamidine, sulfadiazine, clindamycin phosphate, metronidazole, oxacillin sodium, nafcillin sodium, vancomycin hydrochloride, clindamycin, cefotaxime sodium, co-trimoxazole, ticarcillin disodium, piperacillin sodium, ticarcillin disodium/clavulanate potassium, neomycin, daptomycin, cefazolin sodium, cefoxitin sodium, ceftizoxime sodium, penicillin G potassium and sodium, ceftriaxone sodium, ceftazidime, imipenem/cilastatin sodium, aztreonam, cinoxacin, erythromycin/sulfisoxazole, cefotetan disodium, ampicillin sodium/sulbactam sodium, cefoperazone sodium, cefamandole nafate, gentamicin, sulfisoxazole/phenazopyridine, tobramycin, lincomycin, neomycin/polymyxin B/gramicidin, clindamycin hydrochloride, lansoprazole/clarithromycin/amoxicillin, alatrofloxacin, linezolid, bismuth subsalicylate/metronidazole/tetracycline, erythromycin/benzoyl peroxide, mupirocin, fosfomycin, pentamidine isethionate, imipenem/cilastatin, troleandomycin, gatifloxacin, chloramphenicol, cycloserine, neomycin/polymyxin B/hydrocortisone, ertapenem, meropenem, cephalosporins, fluconazole, cefepime, sulfamethoxazole, sulfamethoxazole/trimethoprim, neomycin/polymyxin B, penicillins, rifampin/isoniazid, erythromycin estolate, erythromycin ethylsuccinate, erythromycin stearate, ampicillin trihydrate, ampicillin/probenecid, sulfasalazine, sulfanilamide, sodium sulfacetamide, dapsone, doxycycline hyclate, trimenthoprim/sulfa, methenamine mandelate, plasmodicides, pyrimethamine, hydroxychloroquine, chloroquine phosphate, trichomonocides, anthelmintics, atovaquone, bacitracin, bacitracin/polymyxin b, gentamycin, neomycin/polymyxin/dexameth, neomycin sulf/dexameth, sulfacetamide/prednisolone, sulfacetamide/phenylephrine, tobramycin sulfate/dexameth, bismuth tribromophenate, silver ion compounds, silver nanoparticles, zerovalent silver, multivalent silver, elemental silver, and silver containing compounds such as silver sulfadiazine and related compounds, chlorhexidine and biofilm disrupting agents such as gallium, tryptophan, imidazole derivatives, indole derivatives, emodine, phloretin, isolimonic acid, 7-epiclusianone, casbane diterpene, carvacrol, chelerythrine, ellagic acid, tannic acid, ginkgoneolic acid, resveratrol, viniferin, diphenyl disulfide, S-phenyl-1-cysteine sulfoxide, ajoene, brominated furanones, n-acyl homoserine lactones, skyllamycins, cembranoids, carolacton, etc.

In some embodiments, an antiviral agent is incorporated into the solid lipid particles. Suitable antivirals include but are not limited to, amantadine, acyclovir, foscarnet, indinavir, ribavirin, enfuvirtide, emtricitabine, lamivudine, abacavir sulfate, fomivirsen, valacyclovir, tenofovir, cidofovir, atazanavir, amprenavir, delavirdine mesylate, famciclovir, adefovir, didanosine, efavirenz, trifluridine, inidinavir, lamivudine, vidarabine, lopinavir/ritonavir, ganciclovir, zanamivir, abacavir/lamivudine/zidovudine, lamivudine/zidovudine, nelfinavir, nelfinavir mesylate, nevirapine, ritonavir, saquinavir, saquinavir mesylate, rimantadine, stavudine, docosanol, zalcitabine, idoxuridine, zidovudine, zidovudine/didanosine, valganciclovir, penciclovir, lamivudine, and oseltamivir.

In some embodiments, an antifungal agent is incorporated into the solid lipid particles. Suitable antifungals include but are not limited to, amphotericin B, nystatin, nystatin/triamcinolone, itraconazole, ketoconazole, miconazole, sulconazole, clotrimazole, clotrimazole/betamethasone, enilconazole, econazole, oxiconazole, tioconazole, terconazole, butoconazole, thiabendazole, flucytosine, butenafine, ciclopirox, haloprogin, naftifine, tolnaftate, natamycin, undecylenic acid, mafenide, dapsone, clioquinol, clioquinol/hydrocortisone, potassium iodide, silver sulfadiazine, gentian violet, carbol-fuchsin, cilofungin, sertaconazole, voriconazole, fluconazole, terbinafine, caspofungin, other topical azole drugs, and griseofulvin.

In some embodiments, a buffering agent is incorporated into the solid lipid particles. Suitable buffering agents include but are not limited to In some embodiments, the present invention provides the use and delivery of buffering agents, including, but not limited to, Maleic acid, Phosphoric acid, Glycine, Chloroacetic acid, Formic acid, Benzoic acid, Acetic acid, Pyridine, Piperazine, MES, Bis-tris, Carbonate, ACES, ADA MOPSO, PIPES, Phosphoric acid, BES, MOPS, TES, HEPES, DIPSO, TAPSO, Triethanolamine, HEPSO, Tris, Tricine, Bicine, TAPS, Borate, Ammonia, CHES, Ethanolamine, CAPSO, Glycine, Carbonate, CAPS, Methylamine, Piperidine, and Phosphoric acid.

In some embodiments, a vitamin or mineral is incorporated into the solid lipid particles. Suitable vitamins and minerals include but are not limited to, Vitamin A, Carotenoids, Vitamin D, Vitamin E, Vitamin K, Vitamin C/ascorbic acid, B1/thiamin, B2/riboflavin, B3/niacin, B5/pantothenic acid, B6/pyridoxine, B12/cobalamin, Biotin, Calcium, Magnesium, Phosphorus, Sodium, Chloride, Potassium, Boron, Chromium, Copper, Iodine, Iron, Manganese, Selenium, and Zinc.

In some embodiments, an analgesic agent is incorporated into the solid lipid particles. Suitable analgesics include but are not limited to, acetaminophen, anileridine, acetylsalicylic acid, buprenorphine, butorphanol, fentanyl, fentanyl citrate, codeine, rofecoxib, hydrocodone, hydromorphone, hydromorphone hydrochloride, levorphanol, alfentanil hydrochloride, meperidine, meperidine hydrochloride, methadone, morphine, nalbuphine, opium, levomethadyl, hyaluronate sodium, sufentanil citrate, capsaicin, tramadol, leflunomide, oxycodone, oxymorphone, celecoxib, pentazocine, propoxyphene, benzocaine, lidocaine, dezocine, clonidine, butalbital, phenobarbital, tetracaine, phenazopyridine, sulfamethoxazole/phenazopyridine, and sulfisoxazole/phenazopyridine.

In some embodiments, an anticoagulant agent is incorporated into the solid lipid particles. Suitable anticoagulants include but are not limited to, coumarins, 1,3-indandione, anisindione, fondaparinux, heparin, lepirudin, antithrombin, warfarin, enoxaparin, dipyridamole, dalteparin, ardeparin, nadroparin, and tinzaparin.

In some embodiments, a coagulating agent is incorporated into the solid lipid particles. Suitable coagulating agents include but are not limited to, Factor I (fibrinogen), Factor II (prothrombin), Factor III (thromboplastin, tissue factor), Factor IV (calcium), Factor V (labile factor), Factor VII (stable factor), Factor VIII (antihemophilic globulin, antihemophilic globulin, antihemophilic factor A), Factor IX (plasma thromboplastin component, Christmas factor, antihemophilic factor B), Factor X (Stuart factor, Prower factor, Stuart-Prower factor), Factor XI (plasma thromboplastin antecedent, antihemophilic factor C), Factor XII (Hageman factor, surface factor, contact factor), and Factor XIII (fibrin stabilizing factor, fibrin stabilizing enzyme, fibrinase).

In some embodiments, an anti-inflammatory agent is incorporated into the solid lipid particles. Suitable antiinflammatory agents include but are not limited to NSAIDs such as diclofenac (also known as Voltaren, Abitren, Allvoran, Almiral, Alonpin, Anfenax, Artrites, Betaren, Blesin, Bolabomin, Cataflam, Clofec, Clofen, Cordralan, Curinflam, Diclomax, Diclosian, Dicsnal, Difenac, Ecofenac, Hizemin, Inflamac, Inflanac, Klotaren, Lidonin, Monoflam, Naboal, Oritaren, Remethan, Savismin, Silino, Staren, Tsudohmin, Voltarol, Voren, Voveran, and Vurdon), diflunisal (also known as Dolobid, Adomal, Diflonid, Diflunil, Dolisal, Dolobis, Dolocid, Donobid, Dopanone, Dorbid, Dugodol, Flovacil, Fluniget, Fluodonil, Flustar, Ilacen, Noaldol, Reuflos, and Unisal), etodolac (also known as Lodine), fenoprofen (also known as Nalfon, Fenoprex, Fenopron, Fepron, Nalgesic, and Progesic), flurbiprofen (also known as Ansaid and Ocuflur), ibuprofen (also known as Rufen, Motrin, Aches-N-Pain, Advil, Nuprin, Dolgesic, Genpril, Haltran, Ibifon, Ibren, Ibumed, Ibuprin, Ibupro-600, Ibuprohm, Ibu-Tab, Ibutex, Ifen, Medipren, Midol 200, Motrin-IB, Cramp End, Profen, Ro-Profen, Trendar, Alaxan, Brofen, Alfam, Brufen, Algofen, Brufort, Amersol, Bruzon, Andran, Buburone, Anflagen, Butacortelone, Apsifen, Deflem, Artofen, Dolgit, Artril, Dolocyl, Bloom, Donjust, Bluton, Easifon, Ebufac, Emflam, Emodin, Fenbid, Fenspan, Focus, Ibosure, Ibufen, Ibufug, Ibugen, Ibumetin, Ibupirac, Imbun, Inabrin, Inflam, Irfen, Librofen, Limidon, Lopane, Mynosedin, Napacetin, Nobafon, Nobgen, Novogent, Novoprofen, Nurofen, Optifen, Paduden, Paxofen, Perofen, Proartinal, Prontalgin, Q-Profen, Relcofen, Remofen, Roidenin, Seclodin, Tarein, and Zofen), indomethacin (also known as Indameth, Indocin, Amuno, Antalgin, Areumatin, Argilex, Artherexin, Arthrexin, Artrinovo, Bavilon, Bonidon, Boutycin, Chrono-Indocid, Cidalgon, Confortid, Confortind, Domecid, Durametacin, Elemetacin, Idicin, Imbrilon, Inacid, Indacin, Indecin, Indocap, Indocen, Indocid, Indoflex, Indolag, Indolar, Indomed, Indomee, Indometacinum, Indometicina, Indometin, Indovis, Indox, Indozu, Indrenin, Indylon, Inflazon, Inpan, Lauzit, Liometace, Metacen, Metindon, Metocid, Mezolin, Mobilan, Novomethacin, Peralgon, Reflox, Rheumacid, Rheumacin, Salinac, Servindomet, Toshisan, and Vonum), ketoprofen (also known as Orudis, Alrheumat, Alrheumun, Alrhumat, Aneol, Arcental, Dexal, Epatec, Fastum, Keduril, Kefenid, Keprofen, Ketofen, Ketonal, Ketosolan, Kevadon, Mero, Naxal, Oruvail, Profenid, Salient, Tofen, and Treosin), ketorolac (also known as Toradol), meclofenamate (also known as Meclofen, Meclomen, and Movens), mefenamic acid (also known as Ponstel, Alpain, Aprostal, Benostan, Bonabol, Coslan, Dysman, Dyspen, Ecopan, Lysalgo, Manic, Mefac, Mefic, Mefix, Parkemed, Pondex, Ponsfen, Ponstan, Ponstyl, Pontal, Ralgec, and Youfenam), nabumetone (also known as Relafen), naproxen (also known as Naprosyn, Anaprox, Aleve, Apranax, Apronax, Arthrisil, Artrixen, Artroxen, Bonyl, Congex, Danaprox, Diocodal, Dysmenalgit, Femex, Flanax, Flexipen, Floginax, Gibixen, Headlon, Laraflex, Laser, Leniartil, Nafasol, Naixan, Nalyxan, Napoton, Napren, Naprelan, Naprium, Naprius, Naprontag, Naprux, Napxen, Narma, Naxen, Naxid, Novonaprox, Nycopren, Patxen, Prexan, Prodexin, Rahsen, Roxen, Saritilron, Sinartrin, Sinton, Sutony, Synflex, Tohexen, Veradol, Vinsen, and Xenar), oxaprozin (also known as Daypro), piroxicam (also known as Feldene, Algidol, Antiflog, Arpyrox, Atidem, Bestocam, Butacinon, Desinflam, Dixonal, Doblexan, Dolonex, Feline, Felrox, Fuldin, Indene, Infeld, Inflamene, Lampoflex, Larapam, Medoptil, Novopirocam, Osteral, Pilox, Piraldene, Piram, Pirax, Piricam, Pirocam, Pirocaps, Piroxan, Piroxedol, Piroxim, Piton, Posidene, Pyroxy, Reucam, Rexicam, Riacen, Rosic, Sinalgico, Sotilen, Stopen, and Zunden), sulindac (also known as Clinoril, Aflodac, Algocetil, Antibid, Arthridex, Arthrocine, Biflace, Citireuma, Clisundac, Imbaral, Lindak, Lyndak, Mobilin, Reumofil, Sudac, Sulene, Sulic, Sulindal, Suloril, and Sulreuma), tolmetin (also known as Tolectin, Donison, Midocil, Reutol, and Safitex), celecoxib (also known as Celebrex), meloxicam (also known as Mobic), rofecoxib (also known as Vioxx), valdecoxib (also known as Bextra), aspirin (also known as Anacin, Ascriptin, Bayer, Bufferin, Ecotrin, and Excedrin) and steroidal anti-inflammatory drugs including loteprednol etabonate, cortisone, prednisone and dexamethasone.

In some embodiments, a vasoconstrictor agent is incorporated into the solid lipid particles. Suitable vasoconstrictor agents include but are not limited to, epinephrine (adrenaline, Susphrine), phenylephrine hydrochloride (Neo-Synephrine), oxymetazoline hydrochloride (Afrin), norepinephrine (Levophed), and caffeine.

In some embodiments, a vasodialating agent is incorporated into the solid lipid particles. Suitable vasodialating agents include but are not limited to, bosentan (Tracleer), epoprostenol (Flolan), treprostinil (Remodulin), sitaxsentan, nifedipine (Adalat, Procardia), nicardipine (Cardene), verapamil (Calan, Covera-HS, Isoptin, Verelan), diltiazem (Dilacor XR, Diltia XT, Tiamate, Tiazac, Cardizem), isradipine (DynaCirc), nimodipine (Nimotop), amlodipine (Norvasc), felodipine (Plendil), nisoldipine (Sular), bepridil (Vascor), hydralazine (Apresoline), minoxidil (Loniten), isosorbide dinitrate (Dilatrate-SR, Iso-Bid, Isonate, Isorbid, Isordil, Isotrate, Sorbitrate), isorbide mononitrate (IMDUR), prazosin (Minipress), cilostazol (Pletal), treprostinil (Remodulin), cyclandelate, isoxsuprine (Vasodilan), nylidrin (Arlidin), nitrates (Deponit, Minitran, Nitro-Bid, Nitrodisc, Nitro-Dur, Nitrol, Transderm-Nitro), benazepril (Lotensin), benazepril and hydrochlorothiazide (Lotensin HCT), captopril (Capoten), captopril and hydrochlorothiazide (Capozide), enalapril (Vasotec), enalapril and hydrochlorothiazide (Vaseretic), fosinopril (Monopril), lisinopril (Prinivil, Zestril), lisinopril and hydrochlorothiazide (Prinzide, Zestoretic), moexipril (Univasc), moexipril and hydrochlorothiazide (Uniretic), perindopril (Aceon), quinapril (Accupril), quinapril and hydrochlorothiazide (Accuretic), ramipril (Altace), trandolapril (Mavik), papaverine (Cerespan, Genabid, Pavabid, Pavabid HP, Pavacels, Pavacot, Pavagen, Pavarine, Pavased, Pavatine, Pavatym, Paverolan).

In some embodiments, a diuretic agent is incorporated into the solid lipid particles. Suitable diuretic agents include but are not limited to, acetazolamide (Diamox), dichlorphenamide (Daranide), methazolamide (Neptazane), bendroflumethiazide (Naturetin), benzthiazide (Exna), chlorothiazide (Diuril), chlorthalidone (Hygroton), hydrochlorothiazide (Esidrix, HydroDiuril, Microzide), hydroflumethiazide (Diucardin), indapamide (Lozol), methyclothiazide (Enduron), metolazone (Zaroxolyn, Mykrox), polythiazide (Renese), quinethazone (Hydromox), trichlormethiazide (Naqua), bumetanide (Bumex), ethacrynic acid (Edecrin), furosemide (Lasix), torsemide (Demadex), amiloride (Midamor), amiloride and hydrochlorothiazide (Moduretic), spironolactone (Aldactone), spironolactone and hydrochlorothiazide (Aldactazide), triamterene (Dyrenium), triamterene and hydrochlorothiazide (Dyazide, Maxzide).

In some embodiments, an anticancer agent is incorporated into the solid lipid particles. Suitable anticancer agents include but are not limited to, aldesleukin, alemtuzumab, alitretinoin, allopurinol, altretamine, amifostine, anagrelide, anastrozole, arsenic trioxide, asparaginase, bexarotene, bicalutamide, bleomycin, busulfan, calusterone, capecitabine, carboplatin, carmustine, celecoxib, chlorambucil, cisplatin, cladribine, cyclophosphamide, cytarabine, dacarbazine, dactinomycin, darbepoetin alpha, daunorubicin, daunomycin, dexrazoxane, docetaxel, doxorubicin, epoetin alpha, estramustine, etoposide, etoposide phosphate, exemestane, filgrastim, floxuridine, fludarabine, flutamide, fulvestrant, gemcitabine, gemtuzumab ozogamicin, goserelin acetate, hydroxyurea, ibritumomab tiuxetan, idarubicin, ifosfamide, imatinib mesylate, interferon alpha-2a, interferon alpha-2b, irinotecan, leflunomide, letrozole, leucovorin, levamisole, lomustine, meclorethamine (nitrogen mustard), megestrol acetate, melphalan, mercaptopurine, mesna, methotrexate, methoxsalen, mitomycin C, mitotane, mitoxantrone, mycophenolate mofetil, nandrolone phenpropionate, nilutamide, nofetumomab, oprelvekin, oxaliplatin, paclitaxel, pamidronate, pegademase, pegaspargase, pegfilgrastim, pentostatin, pipobroman, plicamycin, porfimer sodium, procarbazine, quinacrine, rasburicase rituximab, sargramostim, streptozocin, tacrolimus, tamoxifen, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In some embodiments, a trophic agent is incorporated into the solid lipid particles. Suitable trophic agents include but are not limited to, agrin, amphiregulin, artemin, cardiotrophin-1, epidermal growth factors including EGF; fibroblast growth factors (e.g., FGF-1, FGF-2, FGF-3, FGF-4, FGF-5, FGF-6, and FGF-7); LIF, CSF-1, CSF-2, CSF-3, erythropoietin, endothelial cell growth factors including ECGF; FGF- and ECGF-related growth factors (e.g., endothelial cell stimulating angiogenesis factor, tumor angiogenesis factor, retina-derived growth factor (RDGF), vascular endothelium growth factor (VEGF), brain-derived growth factors (BDGF-A and B), astroglial growth factors (AGF 1 and 2), omentum-derived growth factor, insulin like growth factors an fragments such as SSSR, fibroblast-stimulating factor (FSF), and embryonal carcinoma-derived growth factor (ECDGF)); neurotrophic growth factors (e.g, nerve growth factors (NGFs), neurturin, brain-derived neurotrophic factor (BDNF), neurotrophin-3, neurotrophin-4, and ciliary neurotrophic factor (CNTF)); glial growth factors (e.g., GGF-I, GGF-II, GGF-III, glia maturation factor (GMF), and glial-derived neurotrophic factor (GDNF)); liver growth factors (e.g., hepatopoietin A, hepatopoietin B, and hepatocyte growth factors including HGF); prostate growth factors including prostate-derived growth factors (PGFs); mammary growth factors including mammary-derived growth factor 1 (MDGF-1) and mammary tumor-derived factor (MTGF); heart growth factors including non-myocyte-derived growth factor (NMDGF); melanocyte growth factors including melanocyte-stimulating hormone (MSH) and melanoma growth-stimulating activity (MGSA); angiogenic factors (e.g., angiogenin, angiotropin, platelet-derived ECGF, VEGF, and pleiotrophin); transforming growth factors including TGF-α and TGF-β; TGF-like growth factors (e.g., TGF-beta$_1$, TGF-beta$_2$, TGF-beta$_3$, GDF-1, CDGF, tumor-derived TGF-like factors, ND-TGF, and human epithelial transforming factor); regulatory peptides with growth factor-like properties (e.g., bombesin and bombesin-like peptides ranatensin and litorin, angiotensin, endothelin, atrial natriuretic factor, vasoactive intestinal peptide, and bradykinin); platelet-derived growth factors including PDGF-A, PDGF-B, and PDGF-AB; neuropeptides (e.g., substance P, calcitonin gene-regulated peptide (CGRP), and neuropeptide Y); neurotransmitters and their analogs including norepinephrine, acetylcholine and carbachol; hedgehog, heregulin/neuregulin, IL-1, osteoclast-activating factor (OAF), lymphocyte-activating factor (LAF), hepatocyte-stimulating factor (HSF), B-cell-activating factor (BAF), tumor inhibitory factor 2 (TIF-2), keratinocyte-derived T-cell growth factor (KD-TCGF), IL-2, IL-3, IL-4, IL-5, IL-6, IL-7, IL-8, IL-9, IL-10, IL-11, stromal cell-derived cytokine (SCDC), IL-12, IL-13, IL-14, IL-15, insulin, insulin-like growth factors including IGF-1, IGF-2, and IGF-BP; interferons including INF-alpha, INF-beta, and INF-gamma; leptin, midkine, tumor necrosis factors (TNF-alpha and beta), netrins, saposins, semaphorins, somatrem, somatropin, stem cell factor, VVGF, bone morphogenetic proteins (BMPs), adhesion molecules, other cytokines, heparin-binding growth factors, and tyrosine kinase receptor ligands. In some embodiments, the trophic agent is a peptide such as AcEEED, which is the N terminal peptide for alpha smooth muscle actin and has been shown to inhibit contractile properties of myofibroblasts.

In some embodiments, an extracellular matrix (ECM) agent is incorporated into the solid lipid particles. Suitable ECM agents include but are not limited to native constructs, fragments of native constructs and synthetic analogs of: extracellular matrix proteins, reconstituted basement membrane-like complexes derived from eukaryotic cell lines, collagens, fibronectin, laminin, VCAM-1, vitronectin and gelatin, a bacterial extracellular matrix, a gel matrix, and polymeric matrices. In some embodiments, the wound active agents are integrin binding sequences exemplified by, but not limited to RGD, EILDV, VCAM-1 and their recombined or synthetic analogs, enzymes, enzyme inhibitors, and polypeptides.

In some embodiments, an enzyme agent is incorporated into the solid lipid particles. Suitable enzyme agents include but are not limited to, exopeptidases and endopeptidases (also known as proteases and proteinases), including but not limited to the serine proteinases chymotrypsin, trypsin, elastase, and kallikrein, bacterial enzymes, the cysteine proteases papain, actinin, bromelain, cathepsins, cytosolic calpains, parasitic proteases, aspartic proteinases, the pepsin family of proteases pepsin and chymosin, lysosomal cathepsins D, renin, fungal proteases, the viral proteases, AIDS virus retropepsin, and the metalloproteinases (MMPs), collagenases, Maggott enzyme, MMP1, MMP2, MMP8, MMP13, gelatinases, MMP2, MMP9, MMP3, MMP7, MMP10, MMP11, and MMP12.

In some embodiments, an enzyme inhibiting agent is incorporated into the solid lipid particles. Suitable enzyme inhibiting agents include but are not limited to NSAIDS, Aspirin, captopril, thiorphan, phosphoramidon, teprotide, protease and proteinase inhibitors, metalloproteinase inhibitors and exopeptidase inhibitors.

In some embodiments, a polypeptide antimicrobial agent is incorporated into the solid lipid particles. Suitable polypeptide antimicrobial agents include but are not limited to alpha-defensins HNP 1, 2, 3 and 4, and beta-defensins HBD-1, HBD-2, HBD-3, and cathelicidins. Other suitable polypeptide antimicrobial include magainin (e.g., magainin I, magainin II, xenopsin, xenopsin precursor fragment, caerulein precursor fragment), magainin I and II analogs (e.g., PGLa, magainin A, magainin G, pexiganin, Z-12, pexigainin acetate, D35, MSI-78A, MG0 (K10E, K11E, F12W-magainin 2), MG2+(K10E, F12W-magainin-2), MG4+(F12W-magainin 2), MG6+(f12W, E19Q-magainin 2 amide), MSI-238, reversed magainin II analogs (e.g., 53D, 87-ISM, and A87-ISM), Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME(1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 ((+/−) 1-(4-aminobutyl)-6-benzylindane), PM2c ((+/−) -6-benzyl-1-(3-carboxypropyl)indane), PM3 ((+/−)1-benzyl-6-(4-aminobutyl)indane), tachyplesin, buforin I or II, misgurin, melittin, PR-39, PR-26, 9-phenylnonylamine, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG1, 1bAMP, snakin, lipid transfer proteins, and plant defensins. Exemplary sequences for the above compounds are provided in Table 1. In some embodiments, the antimicrobial peptides are synthesized from L-amino acids, while in other embodiments, the peptides are synthesized from, or comprise, D-amino acids.

In some embodiments, a polypeptide agent is incorporated into the solid lipid particles. Suitable polypeptide agents include but are not limited to antibodies and immunoglobulins and fragments thereof, single chain antibodies, humanized antibodies, fibronectin, serotonin, PAF, PDEGF, TNFa, IL1, IL6, IGF, IGF-1, IGF-2, IL-1, PDGF, FGF, KGF, VEGF, bradykinin, prothymosin-alpha, and thymosin-alpha 1.

The micronized lipid particles of the present invention find use in a variety of drug delivery systems and devices.

In some preferred embodiments, the micronized lipid particles are provided in a liquid composition, most preferably an aqueous suspension compatible with mucous membrane surfaces. The term "liquid composition" according to the present invention means any water-containing liquid, solution, or suspension comprising crystalline and amorphous solid low melting temperature micronized particles as described above that may be applied to the human or animal body and that may optionally an active agent or active lipid agent as described in in detail above. In some preferred embodiments, the liquid compositions further comprise excipients, such as, lipids, oils, lipophilic vitamins, lubricants, viscosity agents, acids, bases, antioxidants, stabilizers, synergists, coloring agents, thickening agents, —and if required in a particular cases—a preservative or a surfactant and mixtures thereof.

Useful excipients may be added to the low melting suspended crystalline or amorphous solid in the micronization process and include, but are not limited to, glycerol, propylene glycol, polyethylene glycol, ethanol, acetone, ethyl acetate, isopropyl alcohol, pentylene glycol, liquid paraffin, and triglyceride oils. These added excipients may be therapeutically beneficial or may be added to adjust the melting point or micronized particle size of the low melting suspended solid. Other excipients may be added to the aqueous component of the formulation as viscosity adjustments, stability enhancers and therapeutically beneficial additives.

Useful antioxidants include, but are not limited to, vitamin E or vitamin E derivatives, ascorbic acid, sulphites, hydrogen sulphites, gallic acid esters, butyl hydroxyanisole (BHA), butyl hydroxytoluene (BHT) or acetylcysteine.

In some particularly preferred embodiments, the micronized crystalline or amorphous solid lipid particles are provided in aqueous suspension of an ophthalmically-acceptable vehicle or carrier. Other components, which may be included in the carrier components include, without limitation, buffer components, tonicity components, preservative-components, pH adjustors, viscosity enhancing components commonly found in artificial tears, such as one or more electrolytes, and the like and mixtures thereof. In one very useful embodiment the carrier component includes at least one of the following: an effective amount of a buffer component; an effective amount of a tonicity component; an effective amount of a viscous component, an effective amount of a density component, an effective amount of is a preservative component; and water.

These additional components preferably are ophthalmically acceptable and can be chosen from materials which are conventionally employed in ophthalmic compositions, for example, compositions used to treat eyes afflicted with dry eye syndrome or another eye disorder, artificial tear formulations and the like.

Acceptable effective concentrations for these additional components in the compositions of the invention are readily apparent to the skilled practitioner.

The liquid compositions may be administered, alone, or in combination with pharmaceutically acceptable substances including buffer solutions, for example phosphate buffered saline, or inert carrier compounds, glycerols, mineral oils, waxes or similar substances to the ocular surface of the eye or other mucosal surface as described herein.

The dosage of the above lipid compounds is optimized according to the formulation and method of delivery and the mode of administration is determined by conventional protocols and effectively treats eye disorder symptoms in humans.

The liquid compositions comprising micronized lipid particles may be utilized as a vehicle for topical administration of a therapeutic medicament. Suitable therapeutic medicaments are described above and include active compounds including active lipid compounds. In particular, the liquid compositions of the present invention find use to deliver any desired therapeutic agent, or combination of therapeutic agents, including an active lipid agent, an antibiotic agent, an antiviral agent, an antifungal agent, an anti-cancer agent, an antiglaucoma agent, an antiinflammatory agent, secretagogues exemplified by but not limited to agents that promote lacrimation, salivation or stimulation of release of soluble mucins and or expression of cell associated mucins that promote wettability and/or lubricity of mucosal surfaces, an analgesic, an immunomodulatory agent, a macro-molecule, or a mixture thereof.

In some particularly preferred embodiments, therapeutic agents that may be included the liquid compositions of the present invention, including in the micronized lipid particles in the liquid compositions, include, but are not limited to NMDA antagonists, antihistamines, antiparasitics, miotics, sympathomimetics, anticholinergics, local anesthetics, amoebicidals, trichomonocidals, mydriatics, carbonic anhydrase inhibitors, ophthalmic diagnostic agents, ophthalmic agents used in the treatment of dry eye including by not limited to Xiidra, cyclosporin, corticosteroids and steroids, ophthalmic agents used as adjuvants in surgery, chelating agents, antineoplastics, diagnostics, adrenergic anesthetics, beta blockers, alpha-2-agonists, cycloplegics, prostaglandins, ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline; quinolones such as ciproflaxin, etc.; sulfonamides such as chloramine T; and sulfones such as sulfanilic acid as the hydrophilic entity, anti-viral drugs, e.g. acyclovir, gancyclovir, vidarabine, azidothymidine, dideoxyinosine, dideoxycytosine, dexamethasone, ciproflaxin, water soluble antibiotics, such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, keterolac, naproxen, etc., an anesthetic, e.g. lidocaine; beta-adrenergic blocker or beta-adrenergic agonist, e.g. ephidrine, epinephrine, etc.; aldose reductase inhibitor, e.g. epalrestat, ponalrestat, sorbinil, tolrestat; antiallergic, e.g. cromolyn, beclomethasone, dexamethasone, and flunisolide; colchicine; antiamebic agents, e.g. chloroquine and chlortetracycline; and antifungal agents, e.g. amphotericin, etc., anti-angiogenesis compounds such as anecortave acetate, anti-glaucoma agents, such as brimonidine, acetozolamide, bimatoprost, Timolol, mebefunolol; memantine; alpha-2 adrenergic receptor agonists; 2ME2; anti-neoplastics, such as vinblastine, vincristine, interferons; alpha., beta. and .gamma., antimetabolites, such as folic acid analogs, purine analogs, and pyrimidine analogs; immunosuppressants such as azathiprine, cyclosporin and mizoribine; miotic agents, such as carbachol, mydriatic agents such as atropine, etc., protease inhibitors such as aprotinin, camostat, gabexate, vasodilators such as bradykinin, etc., and various growth factors, such epidermal growth factor, basic fibroblast growth factor, nerve growth factors, and the like, including derivatives thereof and mixtures thereof.

The effective amount micronized lipid particles administered in a liquid composition is specified by routine methods and may be combined with pharmaceutically acceptable substances utilized in ophthalmic vehicles, including buffer solutions, for example phosphate buffered saline, or inert carrier compounds, glycerols, mineral oils or similar substances. The dosage of the micronized lipid particles is optimized according to the formulation and method of delivery and the mode of administration are determined by conventional protocols to effectively treat relevant disorders or symptoms in a subject, for example an eye disorder or other disorder associated with a mucous membrane.

In some preferred embodiments, the liquid compositions comprising the suspended micronized solid lipid particles are administered topically, e.g. as an eye drop. Accordingly, in some preferred embodiments, the liquid compositions comprising micronized lipid particles are stable suspensions of the lipid in the physiologically compatible carrier provided in a container, most preferably a drop dispenser. Suitable drop dispensers are known in the art and include those described in U.S. Pat. Nos. 10,507,132; 10,265,214; 9,999,540; 9,545,333; 7,846,140; 7,563,256; 7,527,613; 6,736,802; 5,810,794; 5,578,020 and 5,558,653; all of which are incorporated by reference herein in their entirety.

In still further embodiments, the liquid compositions comprising micronized liquid or solid lipid particles may be delivered to the ocular surface as a drop from any number of containers including sterile single use containers, blow-fill seal containers, multi-use containers containing preserved or unpreserved micronized suspensions of micronized liquid or solid lipid particles in a aqueous component buffered to pH between 5 and 8, with a concentration of 250-35 mOsmol/L.

In some preferred embodiments, the liquid compositions comprising micronized lipid particles are a suspension of the micronized crystalline or amorphous solid lipid particles. In some preferred embodiments the liquid composition is PBS containing wetting agents and thickening agents to maintain micronized crystalline or amorphous solid lipid particles as a stable suspension in PBS at pH 5-8, osmolality 250 to 350 mOsm/L with a viscosity of 100 or less. In some preferred embodiments, the suspensions comprise buffering agents and may contain a preservative or be preservative free. In some preferred embodiments, the suspensions comprise a stabilizing agent In still other preferred embodiments, the drug delivery vehicle is a medical insert device. As used herein, a medical insert device refers to a solid, three-dimensional structure that is insertable into or onto the body of subject, such as in the eye, vagina, rectum nose, mouth, etc. In some preferred embodiments, the medical insert device is formed from a micronized lipid particles formed into the three-dimensional structure of the device. In other preferred embodiments, the device is formed from a physiologically acceptable material. Suitable physiologically acceptable materials include metals, gels, polymers, proteinaceous materials, and the like. In these embodiments, the device is coated or impregnated with the micronized lipid particles.

In some preferred embodiments, the physiologically acceptable material is a physiologically acceptable polymer. In some preferred embodiments, the physiologically acceptable polymer is selected from the group consisting of hydroxypropyl cellulose, a hydrogel, polymethyl methacrylate, and silicone acrylate. In some embodiments, a bioerodible polymer film suitable for application to the mucosal membranes is preferred such as poly(lactic/glycolic acid-PLGA) and poly(ε-caprolactone). In still other preferred embodiments, the physiologically acceptable polymer is selected from the group consisting of Butyryl-trihexyl-citrate, Di(2-ethylhexyl)phthalate, Di-iso-nonyl-1,2-cyclohexanedicarboxylate, Expanded PTFE, Ethylene vinyl alcohol copolymer, Hexamethylene diisocyanate, High density PE, Highly crosslinked PE, Isophorone diisocyanate, Low density poly(ethylene), Poly(amide), Poly(acrylonitrile), Poly(carbonate), Poly(caprolactone diol), Poly (D-lactic acid), Poly(dimethylsiloxane), Poly(dioxanone), Poly(ethylene), Polyether ether ketone, Poly(ethylene glycol), Poly (ethylene oxide), Polyester polymer alloy, Polyether sulfone, Poly(ethylene terephthalate), Poly(glycolic acid), Poly(hydroxyethyl methacrylate), Poly(lactic-co-glycolic acid), Poly(L-lactic acid), Poly(methyl methacrylate), Poly(methylpentene), Poly(propylene), Polysulfone, Poly(tetrafluoroethylene), Poly(vinyl alcohol), Poly(vinyl chloride), Poly (vinyliden fluoride), Poly(vinylpyrrolidone),Poly(styrene-b-isobutylene-b-styrene), and Ultrahigh molecular weight PE.

The medical insert devices of the present invention may be any shape or size that is compatible with insertion into a desired area of the body of a subject. In some preferred embodiments, the insert is in the shape of a sheet, rod, sphere, partial sphere, tube, cylinder, triangle, cone, etc. In some preferred embodiments, where the insert will be placed into contact with the surface of the eye of a subject, the insert may preferably be a punctal plug, a lens such as a contact lens, or an ophthalmic insert such as a LACRISERT™. In some embodiments, the medical insert device is rechargeable so that micronized lipid particles of the invention may be replenished in the device following use and the device reused. In other preferred embodiments, the device is a single use device.

In some preferred embodiments, the drug delivery devices of the invention find use for delivery of an active agent to a mucosal surface of the body of a subject. Exemplary mucosal surfaces include, but are not limited to an ocular mucosal surface, a vaginal mucosal surface, a cervical mucosal surface, an oviduct mucosal surface, a respiratory system mucosal surface, a nasal mucosal surface, an oropharyngeal mucosal surface, an oral cavity mucosal surface, a rectal mucosal surface, a digestive system mucosal surface, and an esophageal mucosal surface.

In some embodiments, the drug delivery vehicle is applied or administered to a mucosal surface. In some preferred embodiments, the administration is topical. In still other preferred embodiments, the administration is a retrobulbar, intracameral, intravitreal, suprachoroidal and subretinal route of delivery. In some embodiments, the drug delivery vehicle is applied or implanted under the mucosal surface. In some preferred embodiments, the mucosal surface is an ocular mucosal surface and the drug delivery vehicle is implanted or applied under the conjunctival or tenons capsule.

In some preferred embodiments, the active agent is delivered into the body of the subject via the mucosal surface.

In some preferred embodiments, the drug delivery vehicles of the present invention find use in the treatment of a variety of disorder, diseases and conditions. In some preferred embodiments, the disorder, disease or condition is associated with a mucosal surface.

In some preferred embodiments, the present invention provides methods of treating a disease or disorder of the eye selected from the group consisting of dry eye, inflammatory dry eye, evaporative dry eye, meibomian gland dysfunction and symptoms, clinical signs or conditions associated therewith, an unstable tear film resulting in rapid aqueous tear evaporation and keratoconjunctivitis sicca (dry eye) and symptoms or clinical signs associated therewith, in an animal or human subject in need of such treatment. In some preferred embodiments, subjects in need of treatment may be identified by a less than average tear film breakup time measurement. In some preferred embodiments, a therapeutically effective amount of the active agent formulated as a micronized lipid particle is administered to the subject, preferably via a mucosal surface of the eye. In some preferred embodiments, the micronized crystalline or amorphous solid lipid particles are administered to the eye as a suspension in an ophthalmologically acceptable solution. In some preferred embodiments, the micronized crystalline or amorphous solid lipid particles are administered to the eye as a chemically and physically stable suspension in an ophthalmologically acceptable solution with a shelf life at room temperature in excess of 1 day. In some preferred embodiments, the micronized crystalline or amorphous solid lipid particles are administered to the eye as a chemically and physically stable suspension in an ophthalmologically acceptable solution with a shelf life at room temperature in excess of 1 week. In some preferred embodiments, the micronized crystalline or amorphous solid lipid particles are administered to the eye as a chemically and physically stable suspension in an ophthalmologically acceptable solution with a shelf life at room temperature in excess of 1 month. In some preferred embodiments, the micronized crystalline or amorphous solid lipid particles are administered to the eye as a chemically and physically stable suspension in an ophthalmologically acceptable solution with a shelf life at room temperature in excess of 1 year.

In some preferred embodiments, the micronized lipid particles are administered to the eye as a chemically and physically stable suspension in an ophthalmologically acceptable solution with a shelf life at room temperature in excess of 1 day. In some preferred embodiments, the micronized lipid particles are administered to the eye as a chemically and physically stable suspension in an ophthalmologically acceptable solution with a shelf life at room temperature in excess of 1 week. In some preferred embodiments, the micronized lipid particles are administered to the eye as a chemically and physically stable suspension in an ophthalmologically acceptable solution with a shelf life at room temperature in excess of 1 month. In some preferred embodiments, the micronized lipid particles are administered to the eye as a chemically and physically stable suspension in an ophthalmologically acceptable solution with a shelf life at room temperature in excess of 1 year. In still other preferred embodiments, the solid micronized lipid particles release the active lipid agent or other active agents to the tear film including the tear film lipid layer over an extended period of time. In still other preferred embodiments, the solid micronized lipid particles release the active lipid agent or other active agents to the tear film including the tear film lipid layer over a 12 to 24 hour period following a single dose. In still other preferred embodiments, the solid micronized lipid particles release the active lipid agent or other active agents to the tear film including the tear film lipid layer over a 12 to 24 hour period following a single drop applied to the eye surface. In still other preferred embodiments, the solid micronized lipid particles release the active lipid agent or other active agents to the tear film including the tear film lipid layer over a 24 hour period following a single drop of less than 50 microliters in volume. In still other preferred embodiments, the micronized lipid particles are embedded or infused in an insert device capable of releasing the micronized lipid particles to the tear film including the tear lipid layer over an extended period of time. Such devices are exemplified by, but not limited to, punctal plugs, contact lenses, hydroxypropyl cellulose inserts (e.g., LACRISERT™) or other similar devices.

In other preferred embodiments, the drug delivery devices of the present invention find use in treating diseases or disorders associated with disfunction of mucosal membranes including dryness of the mouth, nose, or vagina, vaginal yeast infections, diseases of the respiratory mucous membranes, canker sores, surfactant dysfunction, a polypeptide antimicrobial agent, herpes (caused both by HSV-1 and HSV-2), mucous membrane pemphigoid, oral lichen planus, Sjögren's syndrome, hairy leukoplakia, mucosal pemphigus vulgaris, and chronic aphthous stomatitis. In these embodiments, a therapeutically effective amount of an active agent formulated in a micronized lipid particle is administered to the relevant mucous membrane.

The present invention is not to be limited in scope by the exemplified embodiments, which are only intended as illustrations of specific aspects of the invention. Although there is described hereinabove a specific method of treating mucosal membrane disorders with micronized lipid particles comprising an active agent, in accordance with the present invention for the purpose of illustrating the manner in which the invention can be used to advantage, it will be appreciated that the invention is not limited thereto. For example, the methods and compositions of the present invention may be used to treat other mucosal conditions and disorders that are not listed. Accordingly, any and all variations and modifications which may occur to those skilled in the art are to be considered to be within the scope and spirit of the invention as defined in the appended claims.

EXAMPLES

Example 1—Synthesis of MCAL-201

1-Eicosanyl-2-palmitoyl-rac-glycerol (1,2-EPRG; referred to herein as MCAL-201) manufactured using a process consisting of four discrete chemical steps. The solid drug substance (DS) is further processed by jet-milling to micronized solid particles of 1-10 μm size suitable for suspension in a phosphate buffered saline (PBS) vehicle containing, polysorbate 80 and xanthan gum to stabilize the suspension of micronized particles.

MCAL-201 drug product (DP) is supplied as a sterile unpreserved aqueous suspension of solid micronized (jet milled) MCAL-201 in white, single—use high-density polyethylene (HDPE) dropper vials for direct administration onto the ocular surface as a 35 μL drop.

MCAL-201 is_1-O-eicosanyl-2-palmitoyl-rac-glycerol (1,2-EPRG) and has the following structure:

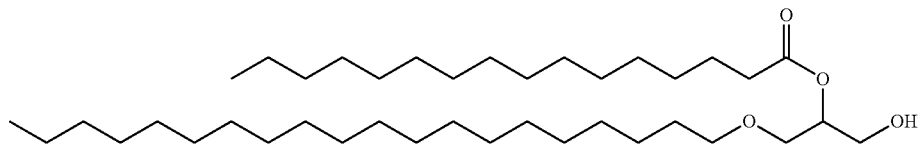 [SMILES: CCCCCCCCCCCCCCCCCCCCOCC(CO)OC(=O)CCCCCCCCCCCCCCC]

The general and physiochemical properties of MCAL-201 are:

1,2-EPRG has a molecular weight of 611.05 g/mol
Empirical formula: $C_{39}H_{78}O_4$
Appearance: White powder
Particle size: 1-10 μm (post micronization)
Hygroscopicity: Low
Chirality: Racemic
Enantiomeric excess: 0
Melting point: 57° C.
Solubility: Insoluble in water. Soluble in chloroform (40 mg/mL) and castor oil (25 mg/mL)

The manufacturing process, through a series of discrete synthetic steps starting with racemic solketal, produces the active pharmaceutical ingredient (API), MCAL-201 as a 1:1 racemic mixture of two enantiomers. The unit operational sequences as shown in FIG. 1.

Figure 2:
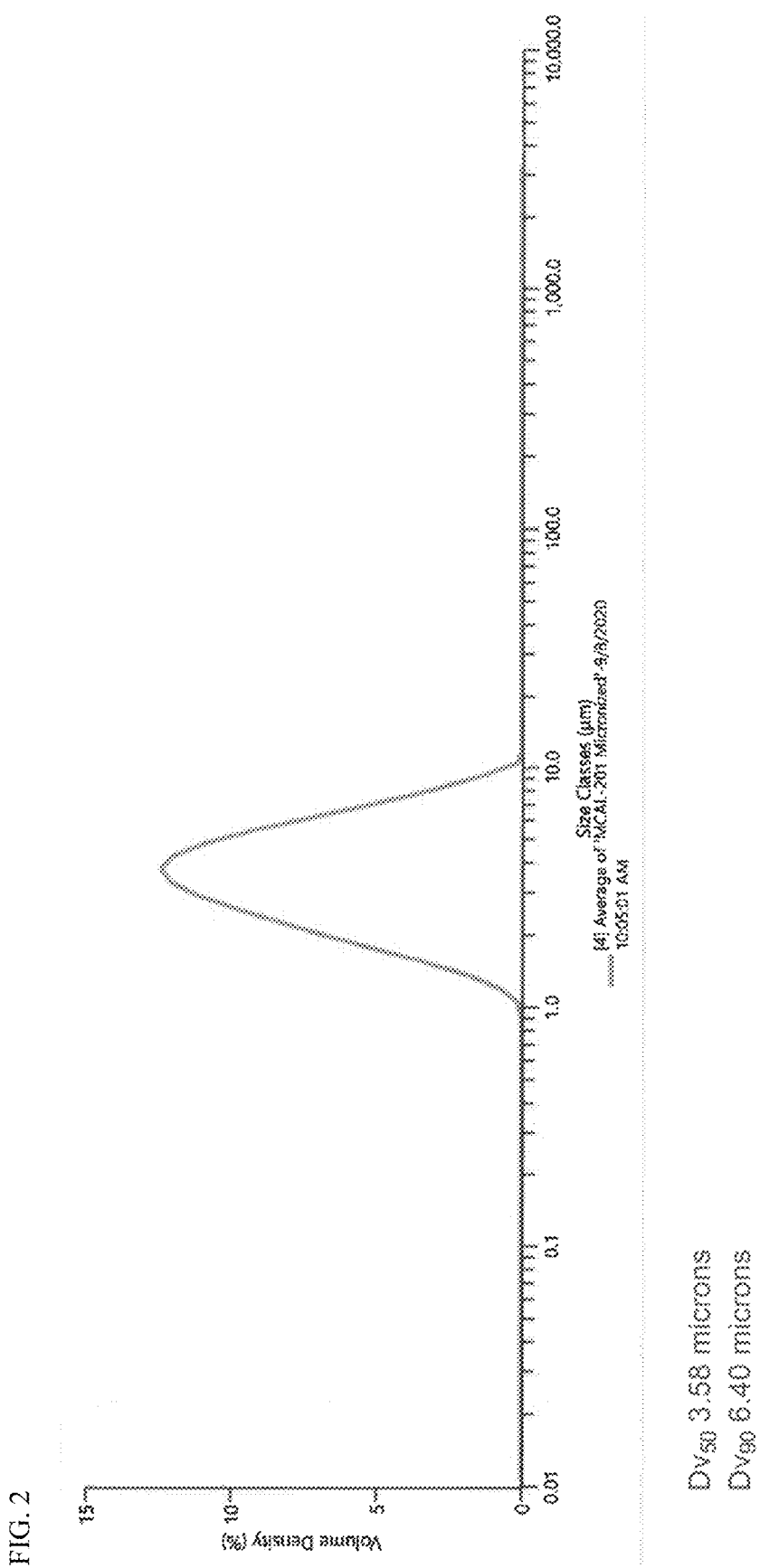
FIG. 2 is a graph showing particle size (assayed by dynamic light scattering) of solid micronized lipid particles of the present invention.

A 420 gram lot of MCAL-201 was manufactured. The Certificate of Analysis (CoA) indicates MCAL 201 drug substance is a 99:1 mixture of 1,2-EPRG and 1,3-EPRG. This lot was used in the nonclinical studies described in further detail herein. Following the synthesis described in FIG. 1, MCAL-201 is further processed by jet-milling or spray drying to achieve a microparticle size range of 1 to 10 microns as determined by dynamic light scattering (DLS) of the micronized solid suspended in PBS (See FIG. 2).

Solubilization of MCAL-201 in aqueous formulations for delivery as an ophthalmic drop without micronization proved to be difficult due to the extreme insolubility of MCAL-201 in water. However, preparation of a water soluble cyclodextrin inclusion complex of MCAL-201 was used in nonclinical efficacy studies. In addition, solutions of MCAL-201 in castor oil which can be emulsified to micron sized liquid particles in aqueous buffers can be used to deliver MCAL-201 directly to the tear film lipid layer.

These cyclodextrin and emulsified castor oil formulations proved to be effective in animal models of dry eye. MCAL- 201 lacked long-term chemical stability in the liquid solution phase with unacceptable levels of acyl migration of the palmitoyl group from the 2 position in MCAL-201 to the more thermodynamically stable 3-position. The isomeric stability of MCAL-201 in the solid phase was observed to be far greater than in solution. This led to development of the delivery of solid MCAL-201 as a suspension of crystalline or amorphous micronized solid particle suspended in a water-based formulation isotonic with tear. Although MCAL-201 crystalline drug substance floated on phosphate buffered saline (PBS) it could be suspended following micronization to 1-10 micron particles which could be stably suspended in PBS with the aid of polysorbate 80 as a wetting agent and xanthan gum to adjust density and viscosity of the drug product.

Example 2—Micronization of MCAL-201

MCAL-201 drug substance is a crystalline solid (m.p. 57° C.) with a flocculent low density texture of powder snow. As such, 50 grams of MCAL-201 drug substance fills a jar designed to hold 500 mL of a more dense liquid or solid such as powdered sugar. Two micronization methods, spray drying and jet milling seem well suited to MCAL-201.

Spray drying method: A solution of MCAL-201 in chloroform (3% w/w) is sprayed into a Buchi B-290 spray dryer in an inert gas flow to create an aerosol with an inlet temperature of 85 degrees over a 10 minute timeframe. This rate is chosen to assure the solid micronized particles form, presumably as amorphous solid particles at least 10 degrees below the crystalline melting point. Micronized particle collection is in a chamber with a cyclonic flow from the pressurized inlet gas to the exit vacuum pressure after much of the solvent (chloroform) has been evaporated and condensed separately. Fifty percent of the injected MCAL-201 formed amorphous micronized solid particles in the collection chamber. Mean particle size was 8.6 microns with a relatively tight size dispersion between 7 and 11 microns, as determined by dynamic light scattering. These particles were dried in vacuuo until residual chloroform was below the limit of quantitation (gas chromatography).

Similarly, a solution of MCAL-201 in chloroform (3% w/w) containing cyclosporin (0.33% w/w) is sprayed into a Buchi B-290 spray dryer in an inert gas flow to create an aerosol with an inlet temperature of 85 degrees over a 10 minute timeframe. Micronized particle collection is in a chamber with a cyclonic flow from the pressurized inlet gas to the exit vacuum pressure after much of the solvent (chloroform) has been evaporated and condensed separately. These particles were dried in vacuuo until residual chloroform was below the limit of quantitation (gas chromatography).

Jet milling method: Crystalline solid MCAL-201 was fed into the spiral mill's grinding chamber under a high velocity gas jet (e.g. super sonic) which induces high energy particle-particle impact and fracturing of the MCAL-201 particles. These particles are constantly swept in a cyclonic flow toward the center of the mill chamber. Particles less than 10 microns are swept into the collection chamber by the cyclonic gas flow. A good amount of MCAL-201 remains stuck to the chamber walls. Three lots of micronized MCAL-201 were prepared below 10 micron mean particle size. All had size distributions between 1 and 15 microns with the smallest particle distribution between 1 and 10 microns. This lot had a mean particle size of 3.56 microns and was taken forward into suspension development studies noted below.

Example 4—Formulation of MCAL-201

MCAL-201 is a non-polar ether lipid initially identified in the secretions of the Harderian gland of rabbits. It is a non-polar lipid of the 1-O-ether, 2-ester glycerol (1,2-EPRG) class associated with the hyperstable tear film lipid layer and long interblink interval (e.g.>20 min) observed in rabbits. MCAL-201 is chemically synthesized under cGMP conditions for use in humans.

MCAL-201 drug product (DP) is a milky white suspension of micronized solid MCAL-201 particles. Each mL of a 0.1% suspension contains 1 mg of the MCAL-201 active ingredient. The drug product can be formulated at 0.0001%, 0.001%, 0.01%, 0.1%, 0.3%, 1% and 5% suspensions of micronized solid MCAL-201. Drug product is aseptically filled into sterile HDPE bottles with a dropper tip that delivers a per drop volume of 35 µL and a protective cap. The drug product is either preserved or unpreserved. The container closure system is sterilized separately prior to filling with DP by gamma irradiation.

An exemplary product batch composition is provided in Table 1.

TABLE 1

GMP Drug Product Batch Composition[1]

| Components | Compendial Grade | DP Formulation |
|---|---|---|
| MCAL-201 (micronized) | NA | 0.001%, 0.01%, 0.1% or TBD |
| PBS (pH 6.8, 280 mOsm/L) | USP | 1 mL |
| Polysorbate 80 | USP | 30 mg/mL |
| Xanthan gum | NF | 0.15 |
| 1N Hydrochloric Acid (HCl) | USP | q.s. |
| 1N Sodium Hydroxide (NaOH) | USP | q.s. |
| Water for injection (WFI) | USP | q.s. |

[1]All excipients used in the MCAL-201 drug product formulation are of non-human or non-animal origin MCAL-201 is formulated at the following strengths: 0.0001%, 0.001%, 0.01%, 0.1%, 0.3% and 1%. Micronized MCAL-201 is mixed with polysorbate-80 as a wetting agent. The appropriate amount of remaining excipients is weighed, dissolved in PBS to a target between 260 to 320 mOsm/L. PBS containing 0.1% to 0.3% (w/v) xanthan gum as a viscosity and density moderating agent is added to the MCAL-201/polysorbate 80 mixture with homogenization to afford a milky white suspension of solid MCAL-201 containing 0.001 to 10 (or TBD) mg/mL of suspended drug. The pH is adjusted with 1N HCl or 1N NaOH to achieve a pH of 6.5-7.2. Final polysorbate 80 concentration is less than or equal to 3% and final xanthan gum concentration is 0.1 to 0.3%. The suspension is analyzed for MCAL-201 content, MCAL-201 isomeric content, particle size distribution, pH, denity and osmolality. Formulated bulk material is aseptically filled into 7.5 mL sterile HDPE bottles including LDPE dropper tips and polypropylene cap closures. Table 2 provides analytical specifications for the drug product.

TABLE 2

Analytical Specifications for MCAL-201 Drug Product

Figure 4:
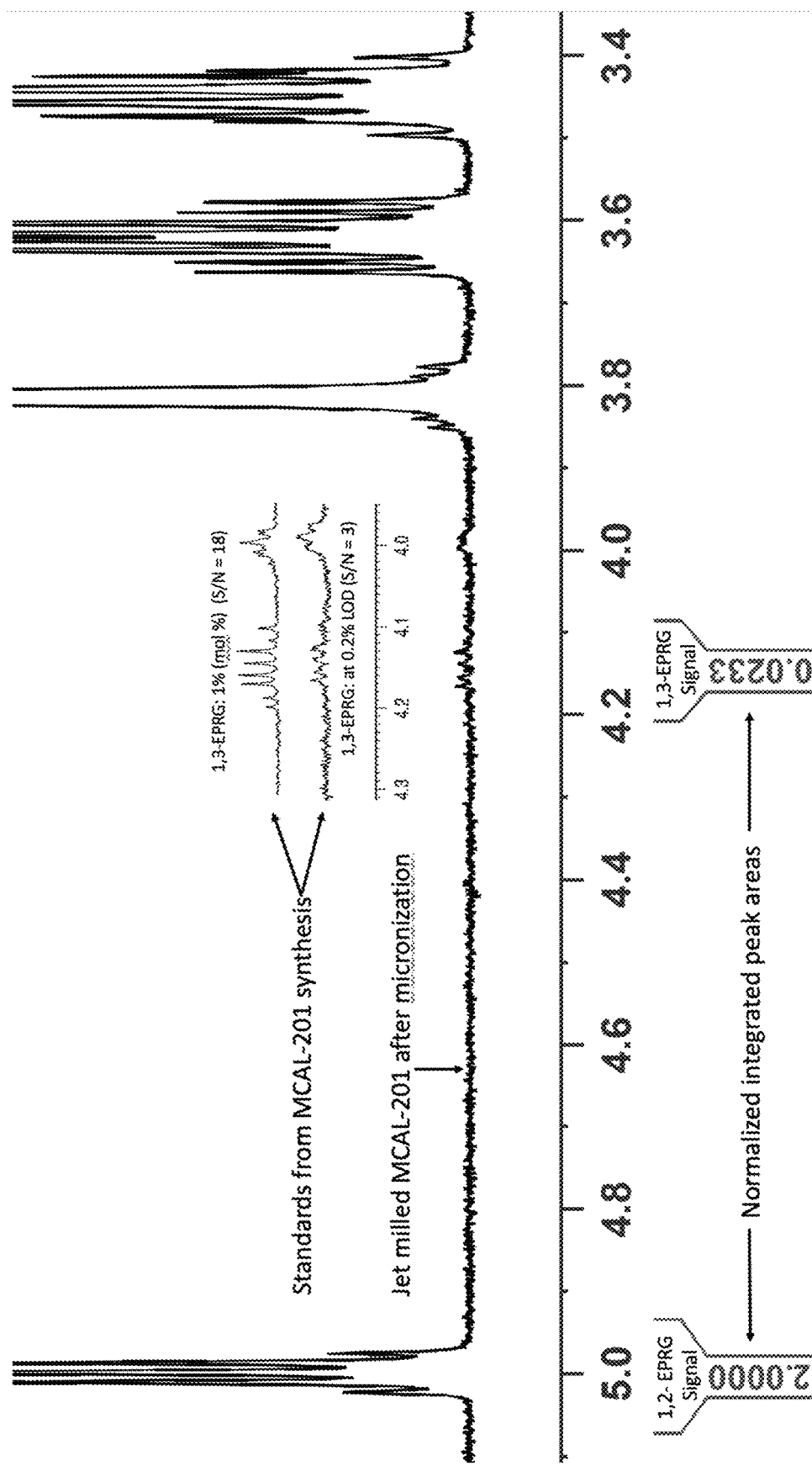
FIG. 4 provides NMR (nuclear magnetic resonance) spectral analysis of 1,3-EPRG and 1,2-EPRG isomeric content (1.15 mol % 1,3-EPRG) of MCAL-201 after jet mill micronization.
Figure 5:
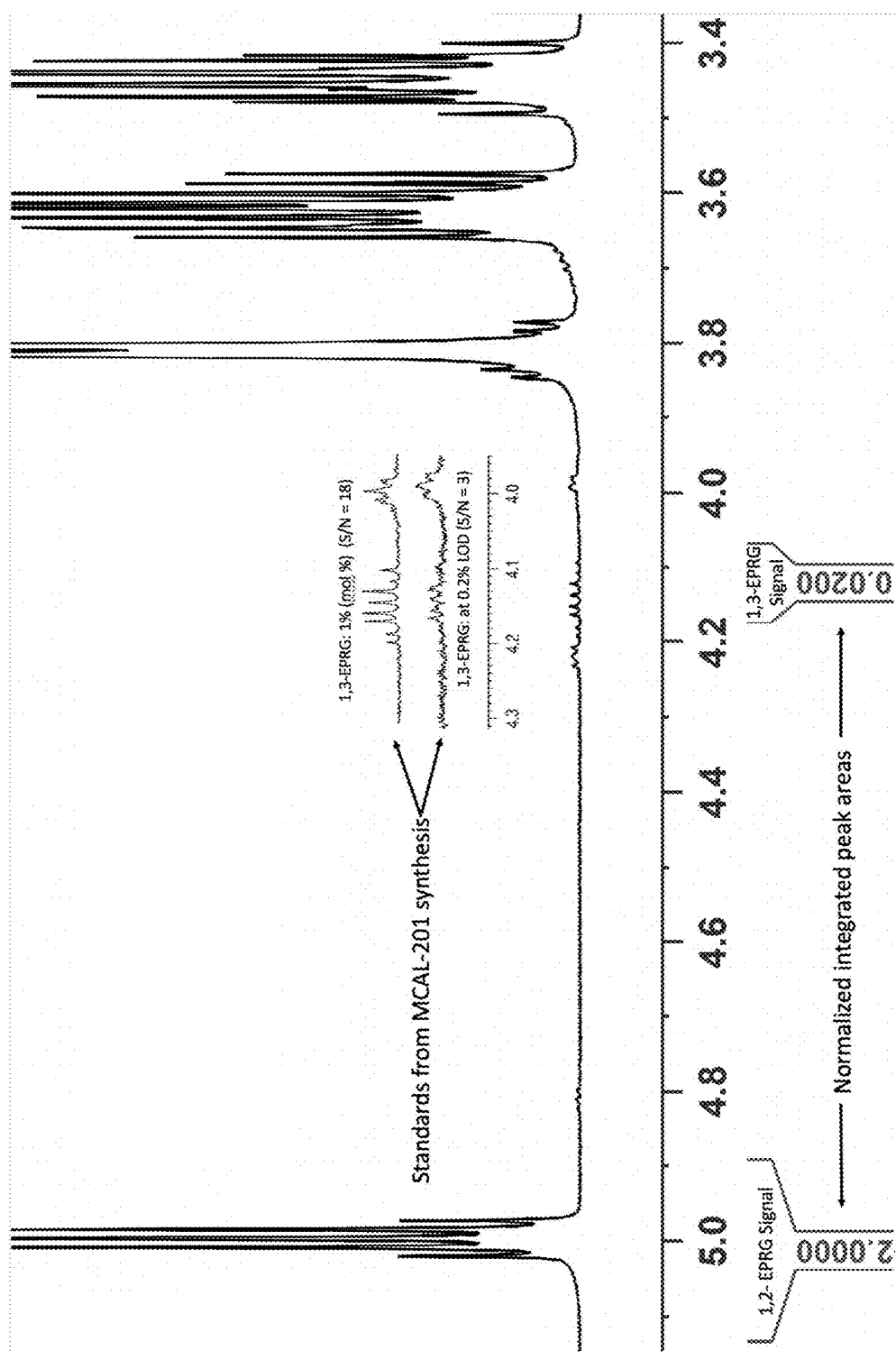
FIG. 5 provides NMR (nuclear magnetic resonance) spectral analysis of 1,3-EPRG and 1,2-EPRG isomeric content (0.0991 mol % 1,3-EPRG) of MCAL-201 after solid micronized MCAL-201suspension is stored at room temperature for 6 weeks.

| Test | Method | Analytical Specification |
| --- | --- | --- |
| Appearance | Visual Assessment | White milky liquid |
| Viscosity | Viscometer | 30-100 cP |
| Particle size | Dynamic Light Scattering | 1-10 μm |
| pH | USP <791> | 6.0-8.0 |
| Osmolality | USP <785> | 230-330 mOsM |
| Sterility | USP <71> | No growth | cP: centipoise,
mOsM: milliosmole,
NMR: nuclear magnetic resonance,
TLC: thin layer chromatography,
USP: United States Pharmacopeia Crystalline MCAL-201 has been micronized to 1-10 micron crystalline and amorphous solid particles (See FIG. 2). Treatment of these particles with poly-sorbate 80 (0.3% w/w) as a wetting agent affords a suspension of the micronized particles in a mixture of xanthan gum (0.1-0.3% w/w, See FIG. 3) in Phosphate Buffered Saline (PBS, pH 6-8, 260-320 mOsm/L) suitable for administration as a stably suspended topical drop or suspension for injection. The physical stability of the micronized suspension toward separation of the micronized particles due to floating, sinking or aggregation of the micronized solid particles has been demonstrated at room temperature for >6 months. Recovery of the micronized solid particles from the formulated drug by centrifugation and washing with water demonstrates chemical and isomeric stability of MCAL-201 to the micronization process (See FIG. 4) and the isomeric stability of micronized MCAL-201 for 6 weeks in the suspension formulation at room temperature (See FIG. 5).

Example 3 — Toxicity and tolerability study

A non-GLP topical ocular administration dose range-finding pharmacology and toxicity study of MCAL-201 was conducted in naive dogs. The primary study objective was to assess the tolerability of topical ocular administration of MCAL-201 in dogs with a secondary objective to obtain data supporting pharmacological activity in healthy dogs.

The effects of vehicle and 0.1, 0.5, 1, 3 and 10 mg/mL MCAL-201 delivered as a 35 μL drop bilaterally QD (0.0035, 0.0175, 0.035, 0.105 and 0.35 mg/eye/day) were evaluated in Part I. The dosing regimen is summarized in 3.

TABLE 3

Dosing Design

| Dog ID | Route of Administration | Dosing Frequency | Dose Level | Dose Concentration (mg/mL) | Volume (μL/eye) |
| --- | --- | --- | --- | --- | --- |
| 1 & 2 | Topical Ocular Drop | QD | MCAL-201 (0.0035-0.35 mg/day/eye) | 0.1-10 | 35 |
| 1 & 2 | Topical Ocular Drop | BID for 2 days | MCAL-201 (0.7 mg/day/eye) | 10 | 35 |

BID: twice daily, QD: once a day.

Ocular endpoints evaluated are summarized in Table 4. Scoring of the ocular surface and anterior segment of the eye was performed using the SPOTS system by a board-certified veterinary ophthalmologist. SPOTS was performed for each concentration evaluated. To measure TBUT, fluorescein was instilled in the eye and the eye was manually closed and then gently opened to simulate a blink. The time interval between the opening of the eye and the first sign of disruption of the uniform tear film, as indicated by breaks in the fluorescein was recorded in seconds. The procedure was repeated three times on both eyes, first right than left eye. After BID dosing with 10 mg/mL MCAL-201, SPOTS was also performed at 48 hours after the last dose.

TABLE 4

Efficacy Endpoints for all Concentrations Tested

| | Time post-dose (hrs) | | | | | | |
| --- | --- | --- | --- | --- | --- | --- | --- |
| Assessment | Pre-dose | 1 | 3 | 6 | 12 | 24 | 48[1] |
| TBUT | X | X | X | X | X | X | X |
| SPOTS | X | X | X | X | X | X | X |
| IOP[1, 2] | X | | | | | X[2] | X[1] |
| STT[1] | X | | | | | | X[1] |

IOP: Intraocular Pressure,
SPOTS: semiquantitative preclinical ocular toxicology scoring,
STT: Schirmer's tear test,
TBUT: Tear Film Break-Up Time
[1]STT and IOP performed at 48 hrs after the last dose of BID delivery of 10 mg/mL MCAL-201.
[2]IOP obtained at 24 hrs post dose for vehicle 0.1, 0.5 and 1.0 mg/mL MCAL-201, and also at 48 hrs post BID treatment with 10 mg/mL MCAL-201.

MCAL-201 was well tolerated and no ocular or systemic adverse events were noted at any time or concentration evaluated (up to 10 mg/mL OU BID for 48 hours). MCAL-201 extended TBUT in 5 healthy adult dogs (FIG. 6).

What is claimed is:

1. A lipid particle composition comprising crystalline solid non-polar lipid particles having an average particle size of less than 50 microns stably suspended in a buffered aqueous vehicle suitable for topical administration, wherein the crystalline solid non-polar lipid particles comprise lipids selected from the group consisting of:

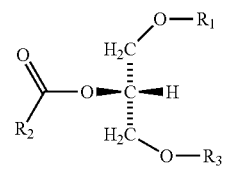

wherein $R_1$ is an unsubstituted C6 to C30 alkyl or alkenyl;

$R_2$ is an unsubstituted C5 to C29 alkyl or alkenyl; and $R_3$ is a hydrogen;

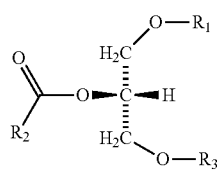

wherein
R₁ is a hydrogen;
R₂ is an unsubstituted C5 to C29 alkyl or alkenyl; and
R₃ is an unsubstituted C6 to C30 alkyl or alkenyl;

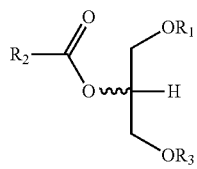

wherein
R₁ is an unsubstituted C6 to C30 alkyl or alkenyl;
R₂ is an unsubstituted C5 to C29 alkyl or alkenyl; and
R₃ is a hydrogen

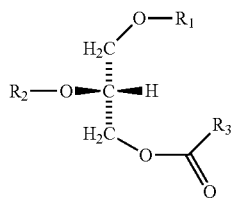

wherein
R₁ is an unsubstituted C6 to C30 alkyl or alkenyl;
R₂ is a hydrogen; and
R₃ is an unsubstituted C5 to C29 alkyl or alkenyl;

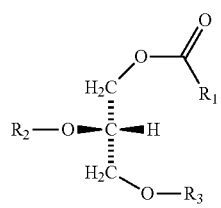

wherein
R₁ is an unsubstituted C5 to C29 alkyl or alkenyl;
R₂ is a hydrogen; and
R₃ is an unsubstituted C6 to C30 alkyl or alkenyl; and

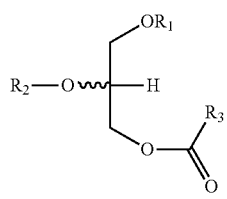

wherein
R₁ is an unsubstituted C6 to C30 alkyl or alkenyl;
R₂ is a hydrogen; and
R₃ is an unsubstituted C5 to C29 alkyl or alkenyl.

2. The lipid particle composition of claim 1, wherein the crystalline solid non-polar lipid particles have a melting point of less than 80 degrees C.

3. The lipid particle composition of claim 1, wherein the crystalline solid non-polar lipid particles have a melting point of from 20 to 80 degrees C.

4. The lipid particle composition of claim 1, wherein the crystalline solid non-polar lipid particles have a melting point of from 30 to 60 degrees C.

5. The lipid particle composition of claim 1, wherein the crystalline solid non-polar lipid particles have an average particle size of less than 20 microns.

6. The lipid particle composition of claim 1, wherein the crystalline solid non-polar lipid particles have an average particle size of less than 10 microns.

7. The lipid particle composition of claim 1, wherein the active lipid agent is a non-polar ether lipid.

8. The lipid particle composition of claim 1, wherein the crystalline solid non-polar lipid particles comprise an active lipid agent selected from the group consisting of 1-O-eicosanyl-2-palmitoyl-rac-glycerol (1,2-EPRG), sn-1-O-eicosanyl-2-palmitoyl-glycerol, sn-2-palmitoyl-3-O-eicosanyl-glycerol, 1-O-eicosanyl-3-palmitoyl-rac-glycerol (1,3-EPRG), sn-1-O-eicosanyl-3-palmitoyl-glycerol, sn-1-palmitoyl-3-O-eicosanyl-glycerol and mixtures thereof.

9. The lipid particle composition of claim 8, wherein the crystalline solid non-polar lipid particles comprise an active lipid agent selected from the group consisting of 1-O-eicosanyl-2-palmitoyl-rac-glycerol (1,2-EPRG) or 1-O-eicosanyl-3-palmitoyl-rac-glycerol (1,3-EPRG) and mixtures thereof.

10. The lipid particle composition of claim 9, wherein the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 95% (mole percent) of the 1-O-eicosanyl-2-palmitoyl-rac-glycerol (1,2-EPRG) isomer or greater than 95% (mole percent) of the 1-O-eicosanyl-3-palmitoyl-rac-glycerol (1,3-EPRG) isomer.

11. The lipid particle composition of claim 9, wherein the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer or greater than 98% (mole percent) of the 1-O-eicosanyl-3-palmitoyl-rac-glycerol (1,3-EPRG) isomer.

12. The lipid particle composition of claim 9, wherein the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer or greater than 99% (mole percent) of the 1-O-eicosanyl-3-palmitoyl-rac-glycerol (1,3-EPRG) isomer.

13. The lipid particle composition of claim 9, wherein the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 95% (mole percent) of the 1-O-eicosanyl-2-palmitoyl-rac-glycerol (1,2-EPRG) isomer and no greater than 5% (mole percent) of the 1-O-eicosanyl-3-palmitoyl-rac-glycerol (1,3-EPRG) isomer.

14. The lipid particle composition of claim 9, wherein the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 98% (mole percent) of the 1-O-eicosanyl-2-palmitoyl-rac-glycerol (1,2-EPRG) isomer and no greater than 2% (mole percent) of the 1-O-eicosanyl-3-palmitoyl-rac-glycerol (1,3-EPRG) isomer.

15. The lipid particle composition of claim 9, wherein the mixture of ether lipid isomers 1-O-eicosanyl-2-palmitoyl-rac-glycerol (1,2-EPRG) and 1-O-eicosanyl-3-palmitoyl-rac-glycerol (1,3-EPRG) is characterized in comprising greater than 99% (mole percent) of the 1-O-eicosanyl-2-palmitoyl-rac-glycerol (1,2-EPRG) isomer and no greater than 1% (mole percent) of the 1-O-eicosanyl-3-palmitoyl-rac-glycerol (1,3-EPRG) isomer.

16. The lipid particle composition of claim 1, wherein the crystalline solid non-polar lipid particles further comprise one or more additional lipids selected from the group consisting of a nonpolar mono-, di-or tri-glyceride, a wax ester including cholesterol esters, a sterol, a free fatty acid and combinations thereof.

17. The lipid particle composition of claim 1, wherein the aqueous buffered vehicle comprises phosphate buffered saline (PBS), 3% or less (w/w of the vehicle) polysorbate 80 and 0.3% or less (w/w of the vehicle) xanthan gum and has a pH of from 6.5-8.0 and an osmolality of from 260 to 320 mOsm/L.

18. The lipid particle composition of claim 1, wherein the suspended particles are stable to phase separation from the suspension for 6 months at room temperature.

19. The lipid particle composition of claim 18, wherein the suspended particles are chemically stable to <5% isomerization of 1,2-EPRG to the isomeric 1,3-EPRG during storage at room temperature for 6 months.

20. The lipid particle composition of claim 1, wherein the suspended particles are stable to phase separation from the suspension for 24 months at room temperature.

21. The lipid particle composition of claim 20, wherein the suspended particles are chemically stable to <5% isomerization of 1,2-EPRG to the isomeric 1,3-EPRG during storage at room temperature for 24 months.

22. The lipid particle composition of claim 1, wherein the composition is sterile.

23. The lipid particle composition of claim 1, wherein the composition comprises a preservative.

24. The lipid particle composition of claim 1, wherein the suspension is preservative-free.

25. The lipid particle composition of claim 1, wherein the aqueous buffered vehicle is an ophthalmologically acceptable carrier.

26. The lipid particle composition of claim 1, wherein the aqueous buffered vehicle further comprises an agent selected from the group consisting of a buffering agent, a tonicity agent, a wetting agent, a thickening and viscosity agent, a density adjusting agent and combinations thereof.

27. The lipid particle composition of claim 1, wherein the active lipid agent in the crystalline solid non-polar lipid particles is released from the crystalline solid non-polar lipid particles as individual molecules for a period of time after administration as an ophthalmic drop.

28. The lipid particle composition of claim 27, wherein the individual molecules are released for a period of from 1 up to 24 hours.

29. The lipid particle composition of claim 1, wherein the suspension is provided in a drop dispenser.

30. A method of treating a disease or disorder of the eye selected from the group consisting of evaporative dry eye, meibomian gland dysfunction and symptoms or conditions associated therewith, an unstable tear film resulting in rapid aqueous tear evaporation and keratoconjunctivitis sicca and symptoms or clinical signs associated therewith, in an animal or human subject in need of such treatment, comprising topically administering a lipid particle composition according to claim 1 comprising an effective amount of the active lipid agent to the eye of the subject.

\* \* \* \* \*